US007442510B2

(12) United States Patent
Miller et al.

(10) Patent No.: US 7,442,510 B2

(45) Date of Patent: Oct. 28, 2008

(54) METHOD OF IDENTIFYING HAIRPIN DNA PROBES BY PARTIAL FOLD ANALYSIS

(75) Inventors: Benjamin L. Miller, Penfield, NY (US); Christopher M. Strohsahl, Saugerties, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 11/553,904

(22) Filed: Oct. 27, 2006

(65) Prior Publication Data

US 2007/0166731 A1 Jul. 19, 2007

Related U.S. Application Data

(63) Continuation of application No. 10/584,875, filed as application No. PCT/US2005/000053 on Jan. 3, 2005.

(60) Provisional application No. 60/533,894, filed on Jan. 2, 2004.

(51) Int. Cl.
*C12Q 1/68* (2006.01)
*C07H 21/02* (2006.01)
*C07H 21/04* (2006.01)

(52) U.S. Cl. .......................... 435/6; 536/23.1; 536/24.3

(58) Field of Classification Search ..................... 435/6; 536/23.1, 24.3
See application file for complete search history.

(56) References Cited

U.S. PATENT DOCUMENTS

| | | | |
|---|---|---|---|
| 5,215,899 A | 6/1993 | Dattagupta | |
| 5,556,749 A | 9/1996 | Mitsuhashi et al. | |
| 5,925,517 A * | 7/1999 | Tyagi et al. | 435/6 |
| 6,114,121 A | 9/2000 | Fujiwara et al. | |
| 6,194,155 B1 | 2/2001 | Cohen | |
| 6,251,588 B1 | 6/2001 | Shannon et al. | |
| 6,277,607 B1 | 8/2001 | Tyagi et al. | |
| 6,312,906 B1 | 11/2001 | Cass et al. | |
| 6,355,437 B1 | 3/2002 | Neri et al. | |
| 6,365,729 B1 | 4/2002 | Tyagi et al. | |
| 6,380,377 B1 | 4/2002 | Dattagupta | |
| 7,070,933 B2 * | 7/2006 | Browne | 435/6 |
| 2003/0013109 A1 | 1/2003 | Ballinger et al. | |
| 2003/0054346 A1 | 3/2003 | Shannon et al. | |
| 2003/0143535 A1 | 7/2003 | Lyamichev et al. | |

FOREIGN PATENT DOCUMENTS

WO 00/43552 A2 7/2000

OTHER PUBLICATIONS

Bonnet et al., "Thermodynamic Basis of the Enhanced Specificity of Structured DNA Probes," *Proc. Natl. Acad. Sci. USA* 96:6171-6176 (1999).

Du et al., "Hybridization-Based Unquenching of DNA Hairpins on Au Surfaces: Prototypical "Molecular Beacon" Biosensors," *J. Am. Chem. Soc.* 125:4012-4013 (2003).

Dubertret et al., "Single-Mismatch Detection Using Gold-Quenched Fluorescent Oligonucleotides," *Nat. Biotech.* 19:365-370 (2001).

Broude, "Stem-loop Oligonucleotides: A Robust Tool for Molecular Biology and Biotechnology," Trends in Biotechnology 20(6):249-56 (2002).

Elsayed et al., "Development and Validation of a Molecular Beacon Probe-Based Real-Time Polymerase Chain Reaction Assay for Rapid Detection of Methicillin Resistance in *Staphylococcus aureus*," Arch. Pathol. Lab. Med. 127:845-9 (2003).

Kushon et al., "Effect of Secondary Structure on the Thermodynamics and Kinetics of PNA Hybridization to DNA Hairpins," J. Am. Chem. Soc. 123(44):10805-13 (2001).

Park et al., "Rapid Identification of *Candida dubliniensis* Using a Species-Specific Molecular Beacon," Journal of Clinical Microbiology 38(8):2829-36 (2000).

Riccelli et al., "Hybridization of Single-stranded DNA Targets to Immobilized Complementary DNA Probes: Comparison of Hairpin Versus Linear Capture Probes," Nucelic Acids Research 29(4):996-1004 (2001).

* cited by examiner

*Primary Examiner*—Ethan Whisenant
(74) *Attorney, Agent, or Firm*—Nixon Peabody LLP

(57) ABSTRACT

Methods of identifying molecular beacons in which a secondary structure prediction algorithm is employed to identify oligonucleotide sequences within a target gene having the requisite hairpin structure. Isolated oligonucleotides, molecular beacons prepared from those oligonucleotides, and their use are also disclosed.

21 Claims, 26 Drawing Sheets

Pag 668 - 706
$E_{predict}$= -4.4 kcal/mol
nt COUNT=39

Pag 1208 - 1241
$E_{predict}$= -4.7 kcal/mol
nt COUNT=34

```
                                                                      Score     E
Sequences producing significant alignments:                          (bits)  Value

gi|20520075|gb|AE011190.1|  Bacillus anthracis str. A2012 pl...        78    7e-13
gi|16031494|emb|AJ413937.1|BAN413937  Bacillus anthracis par...        78    7e-13
gi|16031492|emb|AJ413936.1|BAN413936  Bacillus anthracis par...        78    7e-13
gi|9280532|gb|AF268967.1|AF268967 B acillus anthracis plasmi...        78    7e-13
gi|4894216|gb|AF065404.1|  Bacillus anthracis virulence plas...        78    7e-13
gi|10880952|gb|AF306783.1|  Bacillus anthracis isolate BA102...        78    7e-13
gi|10880950|gb|AF306782.1|  Bacillus anthracis plasmid pX01 ...        78    7e-13
gi|10880948|gb|AF306781.1|  Bacillus anthracis isolate 33 pr...        78    7e-13
gi|10880946|gb|AF306780.1|  Bacillus anthracis isolate BA103...        78    7e-13
gi|10880944|gb|AF306779.1|  Bacillus anthracis isolate 28 pr...        78    7e-13
gi|10880942|gb|AF306778.1|  Bacillus anthracis plasmid pX01 ...        78    7e-13
gi|143280|gb|M22589.1|BACPAG  Bacillus anthracis cryptic pro...        78    7e-13
gi|18308294|gb|AC104301.2|  Homo sapiens chromosome 3 clone ...        42    0.038
gi|19033969|gb|AC069286.7|  Homo sapiens BAC clone RP11-261N...        40    0.15
gi|34849950|gb|AC107065.5|  Bos taurus clone rp42-513g13, co...        40    0.15
gi|30962756|gb|AC137820.11|  Medicago truncatula clone mth2-...        38    0.60
gi|30522931|gb|AC123948.4|  Mus musculus chromosome 10 clone...        38    0.60
gi|22552809|emb|AL671857.16|  Mouse DNA sequence from clone ...        38    0.60
gi|11414543|emb|AL355352.16|  Human DNA sequence from clone ...        38    0.60
gi|7768715|dbj|AP001713.1|  Homo sapiens genomic DNA, chromo...        38    0.60
gi|4827077|dbj|AP000178.1|  Homo sapiens genomic DNA, chromo...        38    0.60
gi|4835635|dbj|AP000266.1|  Homo sapiens genomic DNA, chromo...        38    0.60
gi|3132344|dbj|AP000034.1|  Homo sapiens genomic DNA, chromo...        38    0.60
gi|4730836|dbj|AP000102.1  Homo sapiens genomic DNA of 21q2 ...        38    0.60
gi|3947430|gb|AC003090.1|  Homo sapiens BAC clone CTA-241I2 ...        36    2.4
```

($E_{predict}$= -3.5 kcal/mol)

nt=37

AH2

($E_{predict}$= -6.1 kcal/mol)

nt=33

BaPag668 WITH COMPLEMENT

BaPag1208 WITH COMPLEMENT

AH2 WITH COMPLEMENT

BH2 WITH COMPLEMENT

SEQUENCE LISTING

```
<160> NUMBER OF SEQ ID NOS: 14

<210> SEQ ID NO 1
<211> LENGTH: 960
<212> TYPE: DNA
<213> ORGANISM: Artificial Sequence
<220> FEATURE:
<223> OTHER INFORMATION: Description of Artificial Sequence:  Partial
      gene sequence of Bacillus anthracis pag gene

<400> SEQUENCE: 1

atcttcgaac tcaagaaaaa agcgaagtac aagtgctgga cctacggttc cagaccgtga     60

aagaactttt ctttcaccat ggatttctaa tattcatgaa aagaaaggat taaccaaata    120

taaatcatct cctgaaaaat ggagcacggc ttctgatccg tacagtgatt tcgaaaaggt    180

tacaggacgg attgataaga atgtatcacc agaggcaaga cacccccttg tggcagctta    240

tccgattgta catgtagata tggagaatat tattctctca aaaaatgagg atcaatccac    300

acagaatact gatagtcaaa cgagaacaat aagtaaaaat acttctacaa gtaggacaca    360

tactagtgaa gtacatggaa atgcagaagt gcatgcgtcg ttctttgata ttggtgggag    420

tgtatctgca ggatttagta attcgaattc aagtacggtc gcaattgatc attcactatc    480

tctagcaggg gaaagaactt gggctgaaac aatgggttta aataccgctg atacagcaag    540

attaaatgcc aatattagat atgtaaatac tgggacggct ccaatctaca acgtgttacc    600

aacgacttcg ttagtgttag gaaaaaatca aacactcgcg acaattaaag ctaaggaaaa    660

ccaattaagt caaatacttg cacctaataa ttattatcct tctaaaaact tggcgccaat    720

cgcattaaat gcacaagacg atttcagttc tactccaatt acaatgaatt acaatcaatt    780

tcttgagtta gaaaaaacga aacaattaag attagatacg gatcaagtat atgggaatat    840

agcaacatac aattttgaaa atggaagagt gagggtggat acaggctcga actggagtga    900

agtgttaccg caaattcaag aaacaactgc acgtatcatt tttaatggaa aagatttaaa    960

<210> SEQ ID NO 2
```

-continued

```
<211> LENGTH: 39
<212> TYPE: DNA
<213> ORGANISM: Artificial Sequence
<220> FEATURE:
<223> OTHER INFORMATION: Description of Artificial Sequence:  Hairpin
      probe BaPag668-706 specific for Bacillus anthracis pag gene

<400> SEQUENCE: 2

tttctttcac catggatttc taatattcat gaaaagaaa                           39


<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence:  Hairpin
      probe BaPag1208-1241 specific for Bacillus anthracis pag gene

<400> SEQUENCE: 3

tcgttagtgt taggaaaaaa tcaaacactc gcga                                34


<210> SEQ ID NO 4
<211> LENGTH: 350
<212> TYPE: DNA
<213> ORGANISM: Artificial Sequence
<220> FEATURE:
<223> OTHER INFORMATION: Description of Artificial Sequence:  Partial
      sequence of Staphylococcus aureus genome

<400> SEQUENCE: 4

gaaatgaatg ttacggaaca aacgatgcaa caaaatcatg ctaatttaga ataaaataaa     60

gatagtcgat aatatgatgc ctaggcagaa atattatcga ttattttttt taaattatag    120

tataatatca ataataaacg aataggggtg ttaatattga ttatattttt gattttgatg    180

gtacgttggc agacacgaaa aaatgtggtg acaaagtgca tttaaagcat gtggcttaac    240

ggaaccatca tctaaagaaa tatgggaata cctattgaag aatcattttt aaaattagca    300

gaccgaccat agcattagca aagttaatcg atacatttag acatacatat               350


<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence:  Hairpin
      probe AH2 specific for Staphylococcus aureus genome

<400> SEQUENCE: 5

cgataatatg atgcctaggc agaaatatta tcg                                 33


<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence:  Hairpin
      probe BH2 specific for Staphylococcus aureus genome

<400> SEQUENCE: 6

tatcaataat aaacgaatag gggtgttaat attgata                             37


<210> SEQ ID NO 7
<211> LENGTH: 39
<212> TYPE: DNA
<213> ORGANISM: Artificial Sequence
<220> FEATURE:
```

-continued

```
<223> OTHER INFORMATION: Description of Artificial Sequence:  Complement
      of SEQ ID NO: 2

<400> SEQUENCE: 7

aaagaaagtg gtacctaaag attataagta cttttcttt                              39


<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence:  Complement
      of SEQ ID NO: 3

<400> SEQUENCE: 8

agcaatcaca atccttttt agtttgtgag cgct                                    34


<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence:  Complement
      of SEQ ID NO: 5

<400> SEQUENCE: 9

gctattatac tacggatccg tctttataat agc                                    33


<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence:  Complement
      of SEQ ID NO: 6

<400> SEQUENCE: 10

atagttatta tttgcttatc cccacaatta taactat                                37


<210> SEQ ID NO 11
<211> LENGTH: 49
<212> TYPE: DNA
<213> ORGANISM: Artificial Sequence
<220> FEATURE:
<223> OTHER INFORMATION: Description of Artificial Sequence:  Hairpin
      probe with modified stem

<400> SEQUENCE: 11

cgacgtttct ttcaccatgg atttctaata ttcatgaaaa gaaacgtcg                   49


<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence:  Hairpin
      probe with modified stem

<400> SEQUENCE: 12

cgacgttcac catggatttc taatattcat gaaacgtcg                              39


<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence:  Hairpin
```

-continued

```
      probe with modified stem

<400> SEQUENCE: 13

cgacgtcgtt agtgttagga aaaaatcaaa cactcgcgac gtcg                        44


<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence:  Hairpin
      probe with modified stem

<400> SEQUENCE: 14

cgacgactgt taggaaaaaa tcaaacactc gtcg                                   34
```

METHOD OF IDENTIFYING HAIRPIN DNA PROBES BY PARTIAL FOLD ANALYSIS

CROSS REFERENCE TO RELATED APPLICATIONS

This application is a continuation of U.S. patent application Ser. No. 10/584,875 filed Jun. 29, 2006, which is a national stage application under 35 U.S.C. § 371 of PCT/US2005/000053, filed Jan.3, 2005, and claims the benefit of U.S. Provisional Patent Application Ser. No. 60/533,894, filed Jan. 2, 2004, which is hereby incorporated by reference in its entirety.

This invention was made, at least in part, with funding received from the U.S. Department of Energy under grant DE-FG02-02ER63410.000. The U.S. government may retain certain rights in this invention.

FIELD OF THE INVENTION

The present invention generally relates to the use of DNA hairpins as molecular beacon probes. More specifically, the present invention is directed to methods of generating highly specific and highly selective molecular beacon probes by using naturally occurring DNA hairpins present in organisms of interest.

BACKGROUND OF THE INVENTION

Methods for the rapid detection and serotyping of pathogens are of high interest, due in part to the dramatic improvement in treatment efficacy for a bacterial or viral infection diagnosed early relative to one diagnosed at a later stage (Inglesby et al., "Anthrax as a Biological Weapon: Medical and Public Health Management," *J. Am. Med. Assoc.* 281:1735-1745 (1999)). Unfortunately, most current methods of pathogen identification rely on some level of sample manipulation, (enrichment, fluorescent tagging, etc.) which can be costly in terms of both time and money. Thus, eliminating sample labeling will result in a significant savings and has the potential to speed diagnosis. The use of DNA hairpins as "molecular beacons" (Broude, "Stem-loop Oligonucleotides: a Robust Tool for Molecular Biology and Biotechnology," *Trends Biotechnol.* 20:249-256 (2002)), either in solution (Tyagi et al., "Molecular Beacons: Probes that Fluoresce upon Hybridization," *Nature Biotech.* 19:365-370 (2001); Dubertret et al., "Single-mismatch Detection Using Gold-quenched Fluorescent Oligonucleotides," *Nature Biotech.* 19:365-370 (2001)) or immobilized on a solid surface (Fang et al., "Designing a Novel Molecular Beacon for Surface-Immobilized DNA Hybridization Studies," *J. Am. Chem. Soc.* 121:2921-2922 (1999); Wang et al., "Label Free Hybridization Detection of Single Nucleotide Mismatch by Immobilization of Molecular Beacons on Agorose Film," *Nucl. Acids. Res.* 30:61 (2002); Du et al., "Hybridization-based Unquenching of DNA Hairpins on Au Surfaces: Prototypical "Molecular Beacon" Biosensors," *J. Am. Chem. Soc.* 125:4012:4013 (2003); Fan et al., "Electrochemical Interrogation of Conformational Changes as a Reagentless Method for the Sequence-specific Detection of DNA," *Proc. Natl. Acad. Sci. USA* 100:9134-9137 (2003)), has proven to be a useful method for "label-free" detection of oligonucleotides. Molecular beacons consist of DNA hairpins functionalized at one terminus with a fluorophore and at the other terminus with a quencher. In the absence of their complement, they exist in a closed, "dark" conformation. Hybridization occurs on introduction of complementary oligonucleotides, which concomitantly forces open the hairpin and allows for a fluorescent, "bright" state.

Traditionally, as illustrated in FIG. 1, molecular beacons have been designed by supplementing the targeted DNA sequence at both termini with additional self-complementary nucleotides to force the formation of a hairpin (Monroe et al., "Molecular Beacon Sequence Design Algorithm," *Biotechniques* 34:68-73 (2003)). While generally successful, the addition of non target-derived nucleotides increases the potential for non-specific binding, thus potentially reducing both the sensitivity and selectivity of the probe beacon. Modifications of this discovery protocol, such as the "shared stem" methodology of Bao and coworkers (Tsourkas et al., "Structure-function Relationships of Shared-Stem and Conventional Molecular Beacons," *Nucl. Acids Res.* 30:4208-4215 (2002)), still incorporate several bases unrelated to the target sequence. Thus, the latter approach potentially suffers from the same deficiencies. It would be desirable to identify a reliable approach for identifying DNA hairpins that overcomes the above-noted deficiencies.

The present invention is directed to achieving these objectives and otherwise overcoming the above-noted deficiencies in the art.

SUMMARY OF THE INVENTION

A first aspect of the present invention relates to a method of identifying hairpin nucleic acid probes. The method includes the steps of: providing a target nucleic acid sequence that is larger than about 100 nucleotides in length; predicting a folded structure of the target nucleic acid sequence; identifying the nucleotide sequence of a hairpin within the folded structure of the target nucleic acid sequence; and predicting a folded structure of the identified nucleotide sequence of the hairpin, in the absence of other nucleotides of the target nucleic acid sequence, wherein the folded structure of the hairpin has a predicted E value of at most about −3 kcal/mol.

A second aspect of the present invention relates to a method of preparing a molecular beacon. The method includes the steps of: providing a hairpin nucleic acid probe identified according to the first aspect of the present invention; and tethering a fluorescent label and a quenching agent to the opposed termini of the provided hairpin nucleic acid probe to form a molecular beacon, wherein the molecular beacon is substantially non-fluorescent in the absence of a nucleic acid complementary to the hairpin nucleic acid probe.

A third aspect of the present invention relates to a method of preparing a hairpin nucleic acid molecule. This method includes the steps of identifying the nucleotide sequence of a hairpin in accordance with the first aspect of the present invention; and synthesizing the identified hairpin nucleic acid molecule.

A fourth aspect of the present invention relates to an isolated nucleic acid molecule prepared according to the third aspect of the present invention.

A fifth aspect of the present invention relates to an isolated molecular beacon that includes a nucleic acid molecule according to the fourth aspect of the present invention; a fluorescent label tethered to one terminus of the nucleic acid molecule; and a quenching agent tethered to the other terminus of the nucleic acid molecule.

Additional aspects of the present invention relate to the use of the hairpin nucleic acid molecules and molecular beacons as probes in the detection of target nucleic acid molecules, according to any of a variety of hybridization-based detection procedures.

The ability to rapidly detect the presence of biological agents in the environment is of keen interest to the civilian and military health communities. The use of DNA hairpins as "molecular beacons" has proven a useful method for the detection of bacterial oligonucleotides. The present invention affords a significant improvement over previously employed molecular beacons by using naturally occurring DNA hairpins as molecular beacon probes. This circumvents the need for supplementation with additional bases; as noted in the Examples, supplementation or modification of the naturally occurring hairpins is likely to result in energetically less favorable complementation.

The working examples of the present invention demonstrate the significant specificity and energetically stable target/hairpin dimerizations, thus producing viable molecular beacons for varying experimental conditions, probes and fluorophores. By selecting probes based on their predicted structures and free energy, and by controlling probe length, the present invention affords a systematic approach for preparing nucleic acid probes and molecular beacons that can be used to selectively and sensitively discriminate between target and non-target molecules.

BRIEF DESCRIPTION OF THE DRAWINGS

FIG. 5 demonstrates that the specificity of the BaPag 668-706 hairpin for its target is supported by a BLAST search of the GenBank database using the BaPag 668-706 sequence. A clear demarcation exists between target scores (of 78) and non-target scores (of 42 and lower) indicating that only sequences from *Bacillus anthracis*, the target organism, have high scores; whereas other "matching sequences" from non-target organisms have significantly lower scores.

As seen in FIGS. 13A-C, when immobilized in a 1:1 ratio with mercaptopropanol, BaPag1208 shows a superior response, as measured by fluorescence intensity (y-axis), to target over that observed when the immobilization ratio is 1:10. This increased response is especially significant at lower concentrations as is evidenced by the greater than 20-fold intensity increase observed after incubation in 1.0 μM target (FIGS. 13D-F).

FIG. 16A shows the same secondary structure as in FIG. 4A (SEQ ID NO: 2). The termini of probe BaPag668-706 was extended by the self-complementary sequence $[d(CGACG)]_2$ (SEQ ID NO: 11), then the hybridization energy calculated (FIG. 16B). Five bases were removed from each end of BaPag668-706, replaced with $[d(CGACG)]_2$, and the hybridization energy again calculated (FIG. 16C). BaPag673 corresponds to BaPag668 with 5 bases removed from each end (SEQ ID NO: 12). The complementary sequence of BaPag668-706, in 5'to 3'orientation, is AAAGAAAGTGGTACCT AAAGATTATAAGTACTTTTCTTT (SEQ ID NO: 7). In each case, calculated AAG was less favorable for the modified beacons than for the probes derived directly from folding.

FIG. 17A shows the same secondary structure as in FIG. 4B (SEQ ID NO: 3). The termini of probe BaPag1208-1241 was extended by the self-complementary sequence $[d(CGACG)]_2$ (SEQ ID NO: 13), then the hybridization energy calculated (FIG. 17B). The complementary sequence of BaPag1208-1241, in 5'to 3'orientation, is AGCAATCACAATCCTTTTTTAGTTTGTGAGCGCT (SEQ ID NO: 8). Five bases were removed from each end of BaPag1208-1241, replaced with $[d(CGACG)]_2$ (SEQ ID NO: 14), and the hybridization energy again calculated (FIG. 17C). BaPag1213 corresponds to BaPag1208 with 5 bases removed from each end. In each case, calculated ΔΔG was less favorable for the modified beacons than for the probes derived directly from folding.

DETAILED DESCRIPTION OF THE INVENTION

Figure 1:
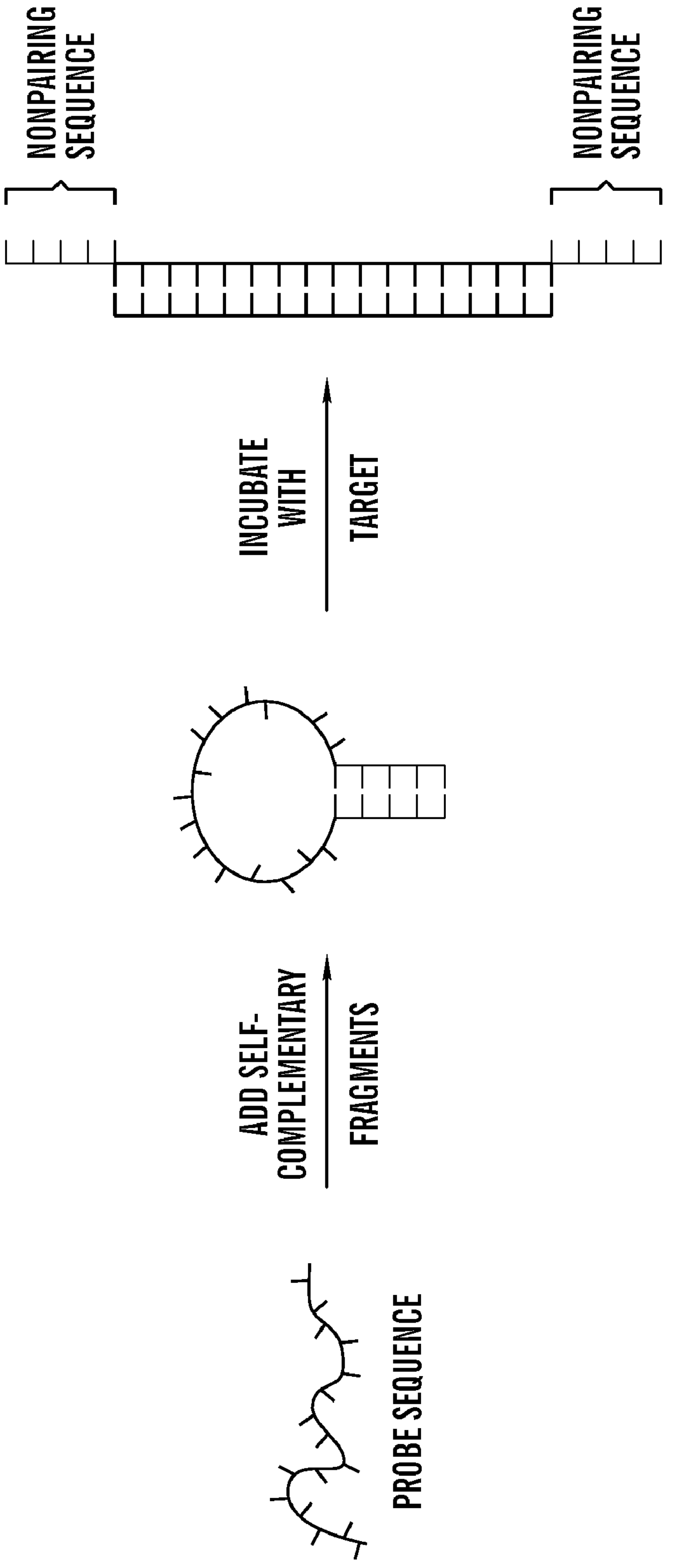
FIG. 1 shows the prior art method of DNA hairpin probe design demonstrating the section of non-pairing sequences present in the final complex.
Figure 2:
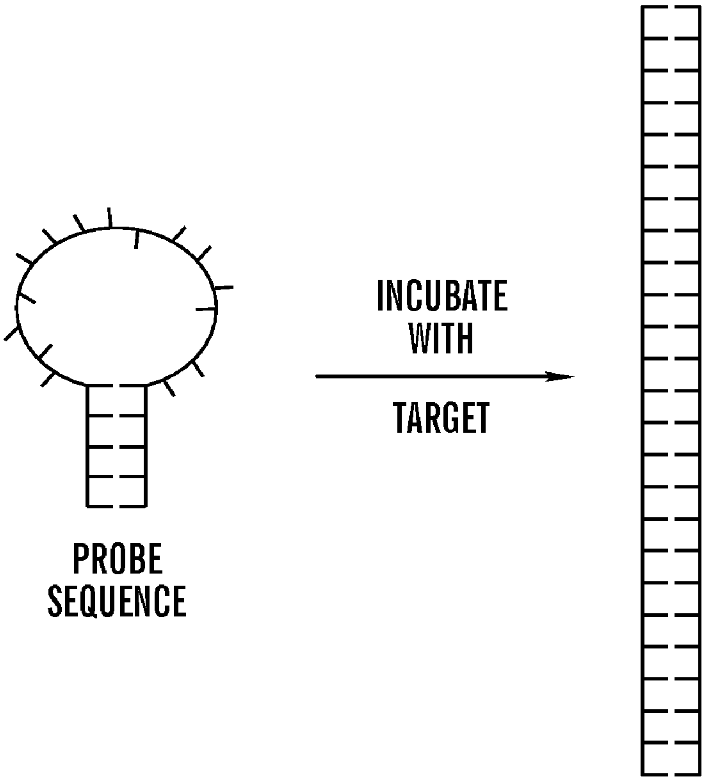
FIG. 2 shows the final probe/target complex of the present invention when the probe is selected based on total sequence complementarity.

The method of the invention involves obtaining or providing a probe nucleotide sequence from a molecular target. The target nucleotide sequence can be sequenced from an isolated cDNA or obtained from an online database such as GenBank. Regardless of the source of the target nucleotide sequence, a partial fold analysis is performed on the nucleotide sequence using any of a variety of suitable folding software such as, e.g., RNAStructure program (available from D. Turner at the University of Rochester, Rochester, N.Y.), Mfold software package (available from M. Zucker at the Rensselear Polytechnic Institute, Rensselear, N.Y.), and Vienna RNA software package, including RNAfold, RNAeval, and RNAsubopt (available from I. Hofacker at the Institute for Theoretical Chemistry, Vienna, Austria). With respect to the RNAStructure program, applicants have discovered that segments larger than approximately 1000 bases would crash the program RNAstructure v. 3.7. Thus, it may or may not be possible to predict the secondary structure of an entire nucleic acid molecule depending on the length thereof. Ideally, the secondary structure of the entire sequence would be predicted, but as demonstrated in the examples that is not necessary.

The resulting folded structure may or may not be the true active conformation of the RNA molecule in a cellular environment; however, it represents the lowest free energy state as predicted using such software. It is believed that more often than not, the predicted lowest free energy state of the nucleic acid molecule sufficiently resembles the true active conformation. Nonetheless, the resulting folded structure is analyzed to identify hairpin regions thereof.

Having identified hairpin structures within the folded structure of the prospective target nucleic acid molecule, the hairpin sequences are isolated from the larger sequence (i.e., that was used as input to the folding software). The isolation can be performed in silico. Once isolated, the hairpin sequence is subjected to a second structural prediction as was performed on the prospective target nucleic acid molecule.

The overall length of the selected hairpin is preferably between about 12 and about 60 nucleotides, more preferably between about 20 and about 50 nucleotides, most preferably between about 30 and about 40 nucleotides. It should be appreciated, however, that longer or shorter nucleic acids can certainly be used. According to the preferred hairpins, the regions forming the stem of the hairpin are preferably at least about 4 nucleotides in length and up to about 28 nucleotides in length, depending on the overall length of the nucleic acid probe and the size of a loop region present between the portions forming the stem. It is believed that a loop region of at least about 4 or 5 nucleotides is needed to form a stable hairpin. The regions forming the stem can be perfectly matched (i.e., having 100 percent complementary sequences that form a perfect stem structure of the hairpin conformation) or less than perfectly matched (i.e., having non-complementary portions that form bulges within a non-perfect stem structure of the hairpin conformation). When the first and second regions are not perfectly matched, the regions forming the stem structure can be the same length or they can be different in length.

Importantly, applicants have found that the predicted E value for the hairpin should preferably be at most about −3 kcal/mol, more preferably at most about −3.5 kcal/mol, most preferably between about −4 kcal/mol and about −12 kcal/mol. It should be appreciated, however, that identified hairpins can still function as molecular probes if their predicted E value falls outside these ranges.

Once the structure of the hairpin itself has been predicted, the duplex formed between the hairpin and its complement is subjected to a structural prediction as was performed on the prospective target nucleic acid molecule and the hairpin. This step, not necessary for identification of the hairpin per se, is performed primarily to ensure that the hybridization of the two sequences (hairpin and complement), and thus the disruption of the hairpin, will be an energetically favorable process. Ideally there should be an increase in the predicted E value preferably at least about a two-fold increase, more preferably at least about a five-fold increase or even more preferably at least about a ten-fold increase. This structural prediction also serves to demonstrate the primary advantage of the technique: after hybridization, there are no extraneous unhybridized nucleotides and, thus, lowered risk of non-specific binding.

To further verify the specificity of the hairpin sequence for its complement, the hairpin sequence can be used to perform a BLAST database search (of, e.g., the GenBank database). Ideally, the resulting BLAST search will show not only high match scores for molecular targets (or target organisms), but also a sharp discrepancy (or clear demarcation) between the high match scores of the target and any match scores of nucleic acid molecules bearing lower similarity. By sharp discrepancy and clear demarcation, it is intended that a gap of at least about 5 points, preferably at least about 10 points, more preferably at least about 15 points, most preferably at least about 20 points, exists between the target and non-target sequences. This is exemplified in Example 1 below.

Having thus identified suitable hairpin nucleic acid molecules that can be utilized for the detection of target nucleic acids and, thus, the identification of target organisms (by virtue of hybridization between the hairpin and the target), persons of skill in the art can readily synthesize hairpin nucleic acid molecules and prepare molecular beacons containing the same in accordance with known procedures.

The hairpin nucleic acid molecules can be synthesized according to standard procedures. Commercial synthesis facilities, in particular, are adept at providing this service.

Molecular beacons can be constructed by tethering to the termini of the hairpin nucleic acid molecule a fluorescent label and a quenching agent, respectively. In one embodiment, the fluorescent label is tethered to the 5' end of the hairpin nucleic acid molecule and the quenching agent is tethered to the 3' end thereof. In another embodiment, the fluorescent label is tethered to the 3' end of the hairpin nucleic acid molecule and the quenching agent is tethered to the 5' end thereof.

The fluorescent label can be any fluorophore that can be conjugated to a nucleic acid and preferably has a photoluminescent property that can be detected and easily identified with appropriate detection equipment. Exemplary fluorescent labels include, without limitation, fluorescent dyes, semiconductor quantum dots, lanthanide atom-containing complexes, and fluorescent proteins. The fluorophore used in the present invention is characterized by a fluorescent emission maxima that is detectable either visually or using optical detectors of the type known in the art. Fluorophores having fluorescent emission maxima in the visible spectrum are preferred.

Exemplary dyes include, without limitation, Cy2™, YO-PRO™-1, YOYO™-1, Calcein, FITC, FluorX™, Alexa™, Rhodamine 110, 5-FAM, Oregon Green™ 500, Oregon Green™ 488, RiboGreen™, Rhodamine Green™, Rhodamine 123, Magnesium Green™, Calcium Green™, TO-PRO™-1, TOTO®-1, JOE, BODIPY® 530/550, Dil, BODIPY® TMR, BODIPY® 558/568, BODIPY® 564/570, Cy3™, Alexa™ 546, TRITC, Magnesium Orange™, Phycoerythrin R&B, Rhodamine Phalloidin, Calcium Orange™, Pyronin Y, Rhodamine B, TAMRA, Rhodamine Red™, Cy3.5™, ROX, Calcium Crimson™, Alexa™ 594, Texas Red®, Nile Red, YO-PRO™-3, YOYO™-3, R-phycocyanin, C-Phycocyanin, TO-PRO™-3, TOTO®-3, DiD DilC(5), Cy5™, Thiadicarbocyanine, and Cy5.5™. Other dyes now known or hereafter developed can similarly be used as long as their excitation and emission characteristics are compatible with a light source and non-interfering with other fluorescent labels that may be tethered to different hairpin nucleic acid molecules (i.e., not capable of participating in fluorescence resonant energy transfer or FRET).

Attachment of dyes to the oligonucleotide probe can be carried out using any of a variety of known techniques allowing, for example, either a terminal base or another base near the terminal base to be bound to the dye. For example, 3'-tetramethylrhodamine (TAMRA) may be attached using commercially available reagents, such as 3'-TAMRA-CPG, according to manufacturer's instructions (Glen Research, Sterling, Va.). Other exemplary procedures are described in, e.g., Dubertret et al., *Nature Biotech.* 19:365-370 (2001); Wang et al., *J. Am. Chem. Soc.*, 125:3214-3215 (2003); *Bioconjugate Techniques*, Hermanson, ed. (Academic Press) (1996), each of which is hereby incorporated by reference in its entirety.

Exemplary proteins include, without limitation, both naturally occurring and modified (i.e., mutant) green fluorescent proteins (Prasher et al., *Gene* 111:229-233 (1992); PCT Application WO 95/07463, each of which is hereby incorporated by reference in its entirety) from various sources such as *Aequorea* and *Renilla*; both naturally occurring and modified blue fluorescent proteins (Karatani et al., *Photochem. Photobiol.* 55(2):293-299 (1992); Lee et al., *Methods Enzymol.* (*Biolumin. Chemilumin.*) 57:226-234 (1978); Gast et al., *Biochem. Biophys. Res. Commun.* 80(1):14-21 (1978), each of which is hereby incorporated by reference in its entirety) from various sources such as *Vibrio* and *Photobacterium*; and phycobiliproteins of the type derived from cyanobacteria and eukaryotic algae (Apt et al., *J. Mol. Biol.* 238:79-96 (1995);

Glazer, *Ann. Rev. Microbiol.* 36:173-198 (1982); Fairchild et al., *J. Biol. Chem.* 269:8686-8694 (1994); Pilot et al., *Proc. Natl. Acad. Sci. USA* 81:6983-6987 (1984); Lui et al., *Plant Physiol.* 103:293-294 (1993); Houmard et al., *J. Bacteriol.* 170:5512-5521 (1988), each of which is hereby incorporated by reference in its entirety), several of which are commercially available from ProZyme, Inc. (San Leandro, Calif.). Other fluorescent proteins now known or hereafter developed can similarly be used as long as their excitation and emission characteristics are compatible with the light source and non-interfering with other fluorescent labels that may be present.

Attachment of fluorescent proteins to the oligonucleotide probe can be carried out using substantially the same procedures used for tethering dyes to the nucleic acids, see, e.g., *Bioconjugate Techniques*, Hermanson, ed. (Academic Press) (1996), which is hereby incorporated by reference in its entirety.

Nanocrystal particles or semiconductor nanocrystals (also known as Quantum Dot™ particles), whose radii are smaller than the bulk exciton Bohr radius, constitute a class of materials intermediate between molecular and bulk forms of matter. Quantum confinement of both the electron and hole in all three dimensions leads to an increase in the effective band gap of the material with decreasing crystallite size. Consequently, both the optical absorption and emission of semiconductor nanocrystals shift to the blue (higher energies) as the size of the nanocrystals gets smaller. When capped nanocrystal particles of the invention are illuminated with a primary light source, a secondary emission of light occurs at a frequency that corresponds to the band gap of the semiconductor material used in the nanocrystal particles. The band gap is a function of the size of the nanocrystal particle. As a result of the narrow size distribution of the capped nanocrystal particles, the illuminated nanocrystal particles emit light of a narrow spectral range resulting in high purity light. Particles size can be between about 1 nm and about 1000 nm in diameter, preferably between about 2 nm and about 50 nm, more preferably about 5 nm to about 20 nm.

Fluorescent emissions of the resulting nanocrystal particles can be controlled based on the selection of materials and controlling the size distribution of the particles. For example, ZnSe and ZnS particles exhibit fluorescent emission in the blue or ultraviolet range (~400 nm or less); Au, Ag, CdSe, CdS, and CdTe exhibit fluorescent emission in the visible spectrum (between about 440 and about 700 nm); InAs and GaAs exhibit fluorescent emission in the near infrared range (~1000 nm), and PbS, PbSe, and PbTe exhibit fluorescent emission in the near infrared range (i.e., between about 700-2500 nm). By controlling growth of the nanocrystal particles it is possible to produce particles that will fluoresce at desired wavelengths. As noted above, smaller particles will afford a shift to the blue (higher energies) as compared to larger particles of the same material(s).

Preparation of the nanocrystal particles can be carried out according to known procedures, e.g., Murray et al., *MRS Bulletin* 26(12):985-991 (2001); Murray et al., *IBM J. Res. Dev.* 45(1):47-56 (2001); Sun et al., *J. Appl. Phys.* 85(8, Pt. 2A): 4325-4330 (1999); Peng et al., *J. Am. Chem. Soc.* 124 (13):3343-3353 (2002); Peng et al., *J. Am. Chem. Soc.* 124 (9):2049-2055 (2002); Qu et al., *Nano Lett.* 1(6):333-337 (2001); Peng et al., *Nature* 404(6773):59-61 (2000); Talapin et al., *J. Am. Chem. Soc.* 124(20):5782-5790 (2002); Shevenko et al., *Advanced Materials* 14(4):287-290 (2002); Talapin et al., *Colloids and Surfaces, A: Physiochemical and Engineering Aspects* 202(2-3):145-154 (2002); Talapin et al., *Nano Lett.* 1(4):207-211 (2001), each of which is hereby incorporated by reference in its entirety. Alternatively, nanocrystal particles can be purchased from commercial sources, such as Evident Technologies.

Attachment of a nanocrystal particle to the oligonucleotide probe can be carried out using substantially the same procedures used for tethering dyes thereto. Details on these procedures are described in, e.g., *Bioconjugate Techniques*, Hermanson, ed. (Academic Press) (1996), which is hereby incorporated by reference in its entirety.

Exemplary lanthanide atoms include, without limitation, Ce, Pr, Nd, Pm, Sm, Eu, Gd, Tb, Dy, Ho, Er, Tm, Yb, and Lv. Of these, Nd, Er, and Tb are preferred because they are commonly used in fluorescence applications. Attachment of a lanthanide atom (or a complex containing the lanthanide atom) to the oligonucleotide probe can be carried out using substantially the same procedures used for tethering dyes thereto. Details on these procedures are described in, e.g., *Bioconjugate Techniques*, Hermanson, ed. (Academic Press) (1996), which is hereby incorporated by reference in its entirety.

The quenching agent can be any agent that can be conjugated to a nucleic acid and preferably is characterized by an absorbance pattern that is matched to cause complete or substantially complete quenching of fluorescence emitted by the fluorescent label. The quenching agent can be another fluorophore that absorbs emissions by the fluorescent label and emits a different fluorescent emission pattern (i.e., during FRET) or the quenching agent can be formed of a material that absorbs fluorescent emissions by the fluorescent label but without a corresponding emission pattern. Examples of the former materials are those described above with respect to the fluorescent label and whose absorption and emission patterns are well suited to achieve FRET. Examples of the latter materials include, without limitation, dyes, such as 4-([4-(Dimethylamino)phenyl]azo)benzoic acid (dabcyl); and metals such as gold, silver, platinum, copper, cobalt, iron, iron—platinum, etc. Of these, the dye dabcyl and the metals gold, silver, and platinum are typically preferred.

The quenching agent can either be in the form of a small molecule such as a dye, a particle such as a micro- or submicron-sized (i.e., nano-) particle, or in the form of a substrate that contains thereon a sufficient density of the quenching agents such that the surface thereof is effectively a quenching surface. In one embodiment, the quenching agent is a dye or a metal nanoparticle. In another embodiment, a substrate having a quenching metal surface is utilized, such as a substrate bearing a gold film thereon.

Assembly of the hairpin probe, e.g., on the metal surface, is carried out in the presence of a spacing agent. Preferred spacing agents are non-nucleic acid thiols. Exemplary spacing agents include, without limitation, 3-mercapto-1-propanol, 1-mercapto-2-propanol, 2-mercaptoethanol, 1-propanethiol, 1-butanethiol, 1-pentanethiol, 3-mercapto-1,2-propanediol, 1-heptanethiol, 1-octanethiol, and 1-nonanethiol. Ratios of non-nucleic acid thiol:DNA hairpin employed in the assembly process are typically about 1:1 or greater, more preferably about 5:1 or greater. It is believed that the spacing agent provides spacing between individual molecules of DNA hairpin on the metal surface. Chips assembled in the absence of spacing agent are, at best, poorly functional.

When multiple molecular beacons are used (e.g., in a microarray or other similar format) and each is conjugated to a fluorescent label, it is preferable that the fluorescent labels can be distinguished from one another using appropriate detection equipment. That is, the fluorescent emissions of one fluorescent label should not overlap or interfere with the fluorescent emissions of another fluorescent label being utilized. Likewise, the absorption spectra of any one fluorescent label should not overlap with the emission spectra of another fluorescent label (which may result in undesired FRET that can mask emissions by the other label).

The probes and molecular beacons identified in accordance with the present invention can be used in any of a variety of hybridization-based applications, typically though not exclusively detection procedures for identifying the presence in a sample of a target nucleic acid molecule. By way of example, uses of the probes and molecular beacons are described in greater detail in PCT Patent Application to Miller et al., entitled "Hybridization-Based Biosensor Containing Hairpin Probes and Use Thereof," filed Jan. 2, 2003, now WO 2004/061127, which is hereby incorporated by reference in its entirety.

EXAMPLES

The Examples set forth below are for illustrative purposes only and are not intended to limit, in any way, the scope of the present invention.

Example 1

Hairpins Targeted to *Bacillus anthracis* pag Gene

Figure 3:
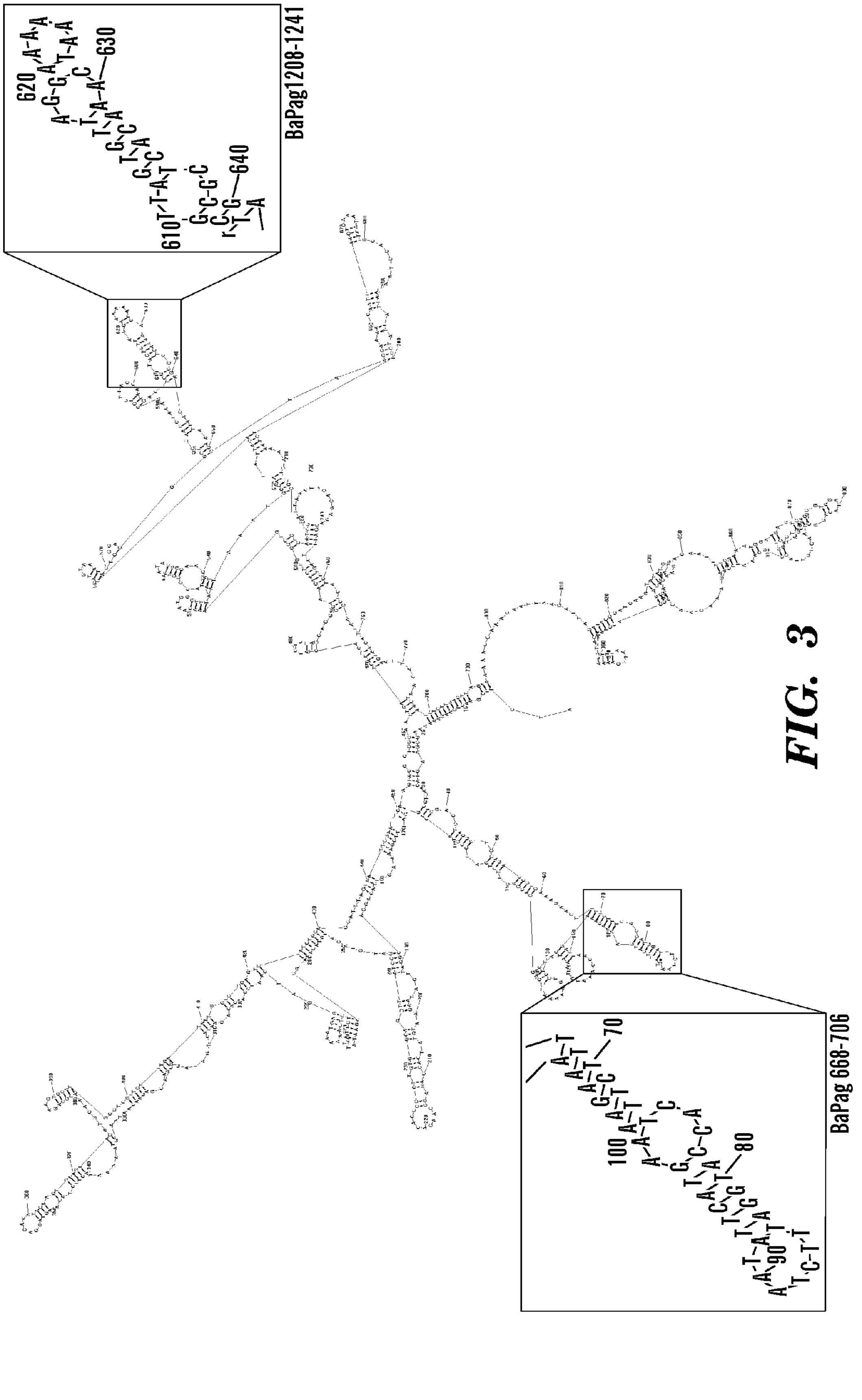
FIG. 3 shows the predicted secondary structure and hairpin regions selected from *Bacillus anthracis*. A partial gene sequence of the *Bacillus anthracis* pag gene (isolate IT-Carb3-6254) (Adone et al., *J. Appl. Microbiol.* 92:1-5 (2002), which is hereby incorporated by reference in its entirety) was obtained from GenBank Accession AJ413936, which is hereby incorporated by reference in its entirety. The secondary structure of ~1000 nucleotide fragment (SEQ ID NO: 1) of the aforementioned sequence was then computationally predicted using RNAstructure v. 3.7 (Mathews et al., *J. Mol. Biol.* 288:911-940 (1999), which is hereby incorporated by reference in its entirety).
Figure 4A:
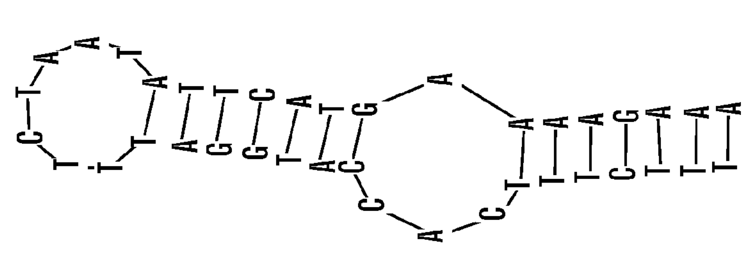
FIGS. 4A-B show structural predictions for two excised sequences: BaPag668-706 (Pag668-706) (SEQ ID NO: 2) and BaPag1208-1241(Pag1208-1241) (SEQ ID NO: 3). The sequences are isolated from the full sequence and subjected to secondary structure predictions. The number of nucleotides is indicated by nt count.
Figure 4B:
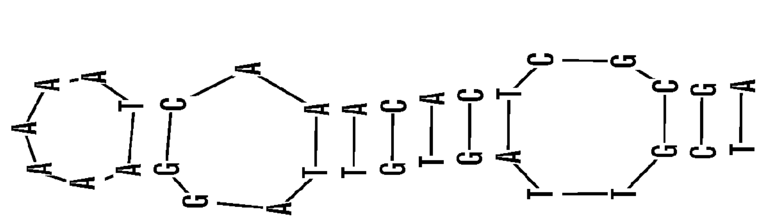

A large sequence structure prediction from *Bacillus anthracis* is shown in FIG. 3 and depicts the "folding" of large sequences of DNA revealing several naturally occurring hairpins. The sequences are then isolated from the full sequence and subjected to second structure prediction. FIGS. 4A-B show structural predictions for two of these excised sequences.

These natural hairpins, BaPag668-706 (Pag 668) and BaPag1208-1241 (Pag 1208), both appear to be good candidates for use as a molecular beacon, because each contains between about 30 to about 40 nucleotides and each has a $E_{predict}$ between about −4 kcal/mol and about −12 kcal/mol.

Figure 8A:
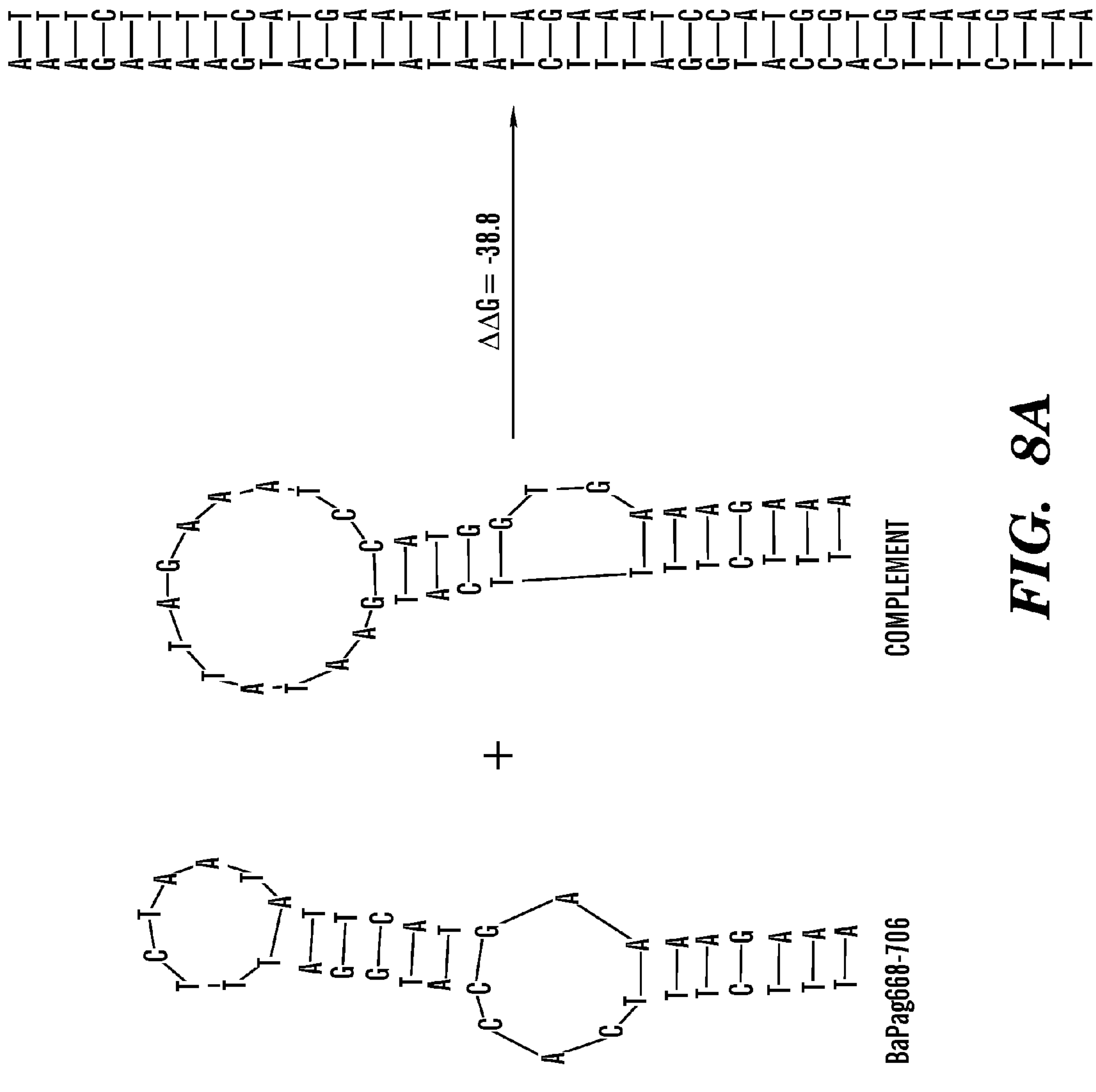
FIGS. 8A-D show the final structural prediction of BaPag 668-706 (SEQ ID NO: 2), BaPag 1208-1241 (SEQ ID NO: 3), AH2 (SEQ ID NO: 5), and BH2 (SEQ ID NO: 6) in duplex with their corresponding complements (SEQ ID NOS: 7-10, respectively). Having confirmed that the selected hairpin(s) satisfy initial selected criteria, a final structural prediction of the sequence in duplex with its complement was computed. Each of these duplexes have a predicted E value that is about nine to ten-fold greater than the predicted E value (or ΔΔG value) for the hairpin alone, and therefore they are expected to favorably form a duplex with their targets.
Figure 8B:
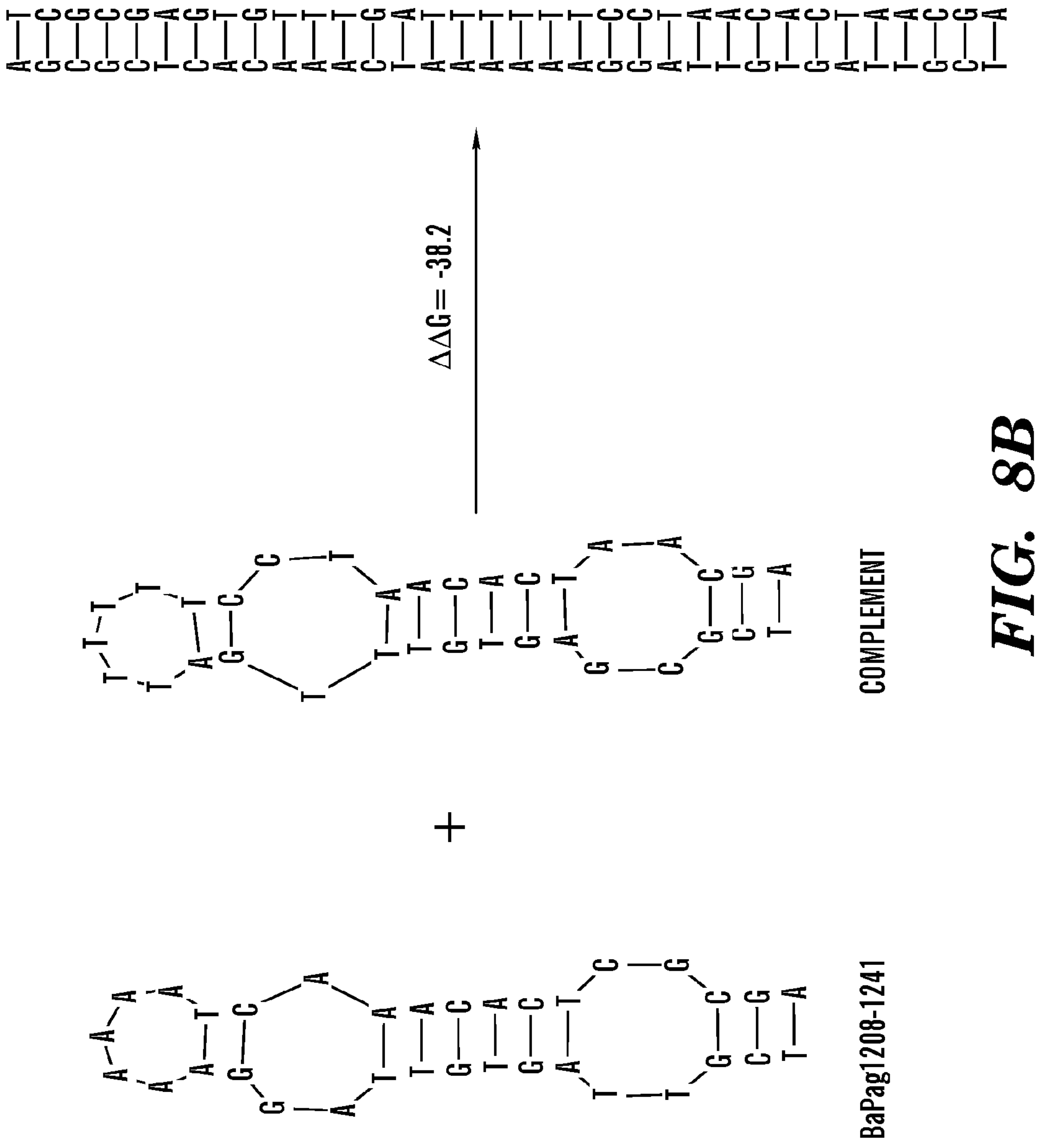

Having confirmed that the selected hairpin(s) satisfy initial selection criteria, a final structural prediction of the sequence in duplex with its complement was computed (FIGS. 8A-B). This last prediction was done primarily to ensure that the hybridization of the two DNA sequences, and thus the disruption of the hairpin will be an energetically favorable process. Each of these duplexes have a predicted ΔΔG value that is about nine to ten-fold greater than the predicted E (ΔG) value for the hairpin alone, and therefore they are expected to favorably form a duplex with their targets.

The specificity of the hairpin of FIG. 4 for its target was supported by a BLAST search of the GenBank database using the BaPag 668-704 sequence. The results of this BLAST search are shown below in FIG. 5. In particular, the BLAST results indicate that only sequences from *Bacillus anthracis*, the target organism, have high scores; whereas other "matching sequences from non-target organisms have significantly lower scores. In this instance, a clear demarcation exists between target scores (of 78) and non-target scores (of 42 and lower). This demonstrates that this hairpin will be specific for its target.

Example 2

Hairpins Targeted to *Staphylococcus aureus* Genome

Two DNA hairpins, AH2 and BH2, were designed to incorporate portions of the *Staphylococcus aureus* genome (Genbank Accession AP003131, which is hereby incorporated by reference in its entirety). The AH2 sequence appears to target an intergenic region between ORFID:SA0529 and ORFID:SA0530, and the BH2 sequence appears to target an intergenic region between ORFID:SA0529 and ORFID:SA0530 but also includes several bases within the latter open reading frame.

Figure 6:
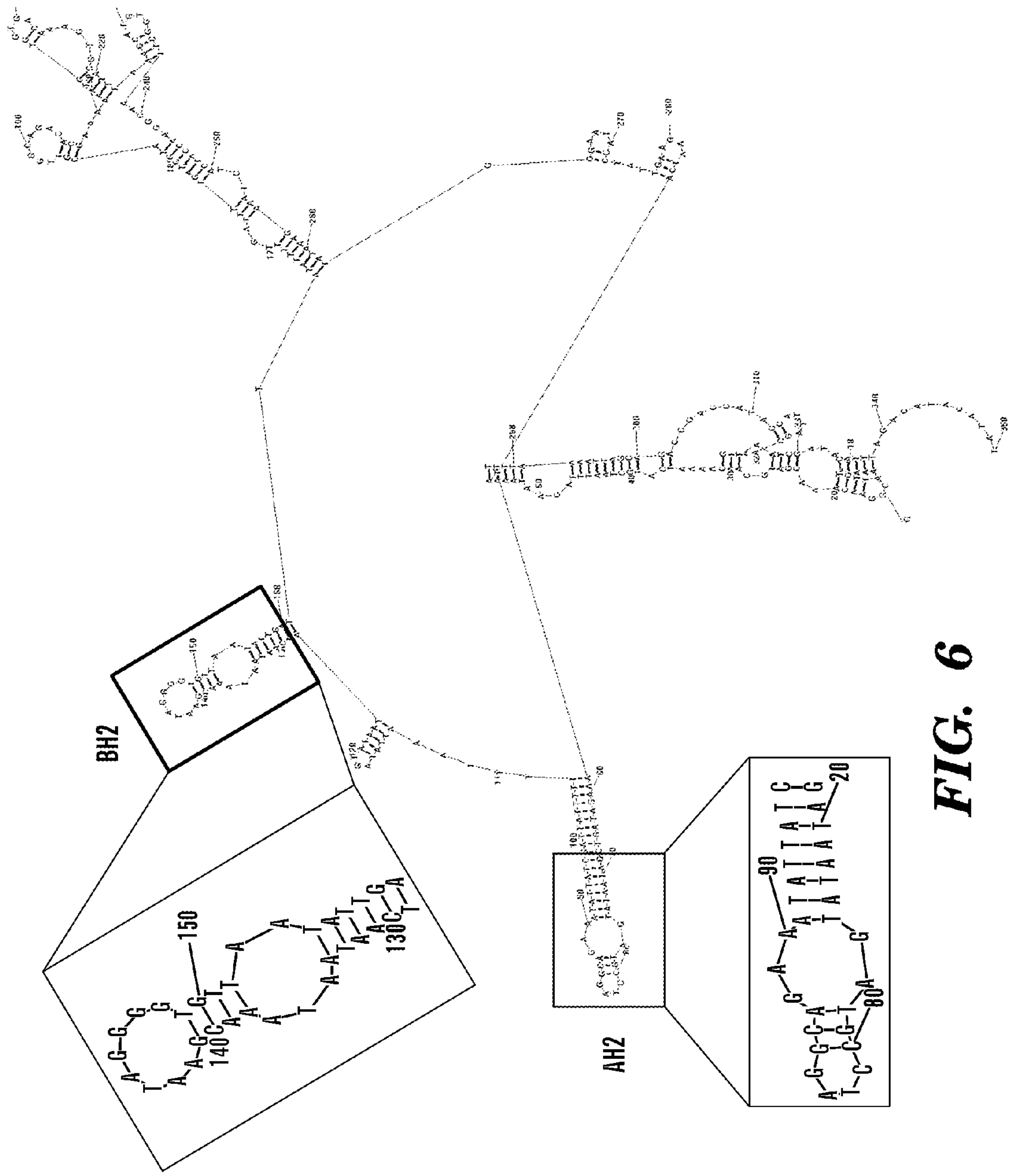
FIG. 6 shows the predicted secondary structure and hairpin regions selected from the *Staphylococcus aureus* genome, a segment of which (SEQ ID NO: 4) was obtained from Genbank Accession AP003131, which is hereby incorporated by reference in its entirety. The secondary structure of the obtained segment was predicted using computer program RNAStructure version 3.7 (Mathews et al., *J. Mol. Biol.* 288: 911-940 (1999), which is hereby incorporated by reference in its entirety). From this predicted structure, two naturally occurring hairpins were identified, one corresponding to AH2 and the other corresponding to BH2.

A segment of the complete *Staphylococcus aureus* genome was obtained from the GenBank database and the secondary structure of the obtained segment was predicted using computer program RNAStructure version 3.7 (Mathews et al., *J. Mol. Biol.* 288:911-940 (1999), which is hereby incorporated by reference in its entirety), as shown in FIG. 6. From this predicted structure, two naturally occurring hairpins were identified, one designated AH2 and the other designated BH2 (FIG. 6).

Figure 7B:
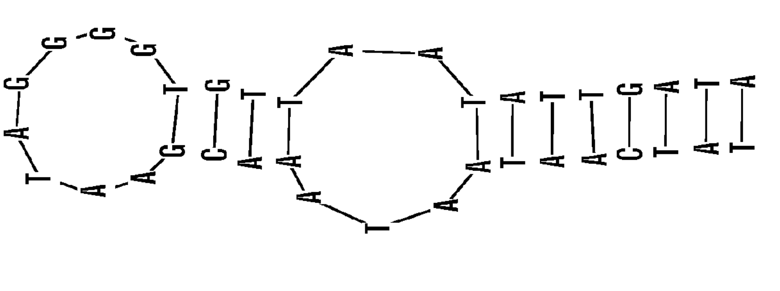
FIGS. 7A-B show structural predictions for two excised sequences: AH2 (SEQ ID NO: 5) and BH2 (SEQ ID NO: 6). The sequences were isolated from the full sequence and subjected to second structure predictions. The AH2 sequence appears primarily to target an intergenic region between ORFID:SA0529 and ORFID:SA0530, and the BH2 sequence appears to target an intergenic region between ORFID: SA0529 and ORFID:SA0530 but also includes several bases within the latter open reading frame.
Figure 7A:
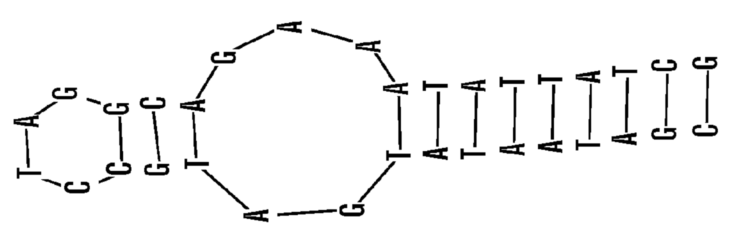

Having identified these two sequences, these sequences were isolated from the larger sequence and subjected to a second structure prediction as described above. The predicted structure of AH2 is characterized by a predicted free energy value of about −6.1 kcal/mol (FIG. 7A) and the predicted structure of BH2 is characterized by a predicted free energy value of about −3.5 kcal/mol (FIG. 7B). Both are within the size range of about 30-40 nucleotides.

Figure 8C:
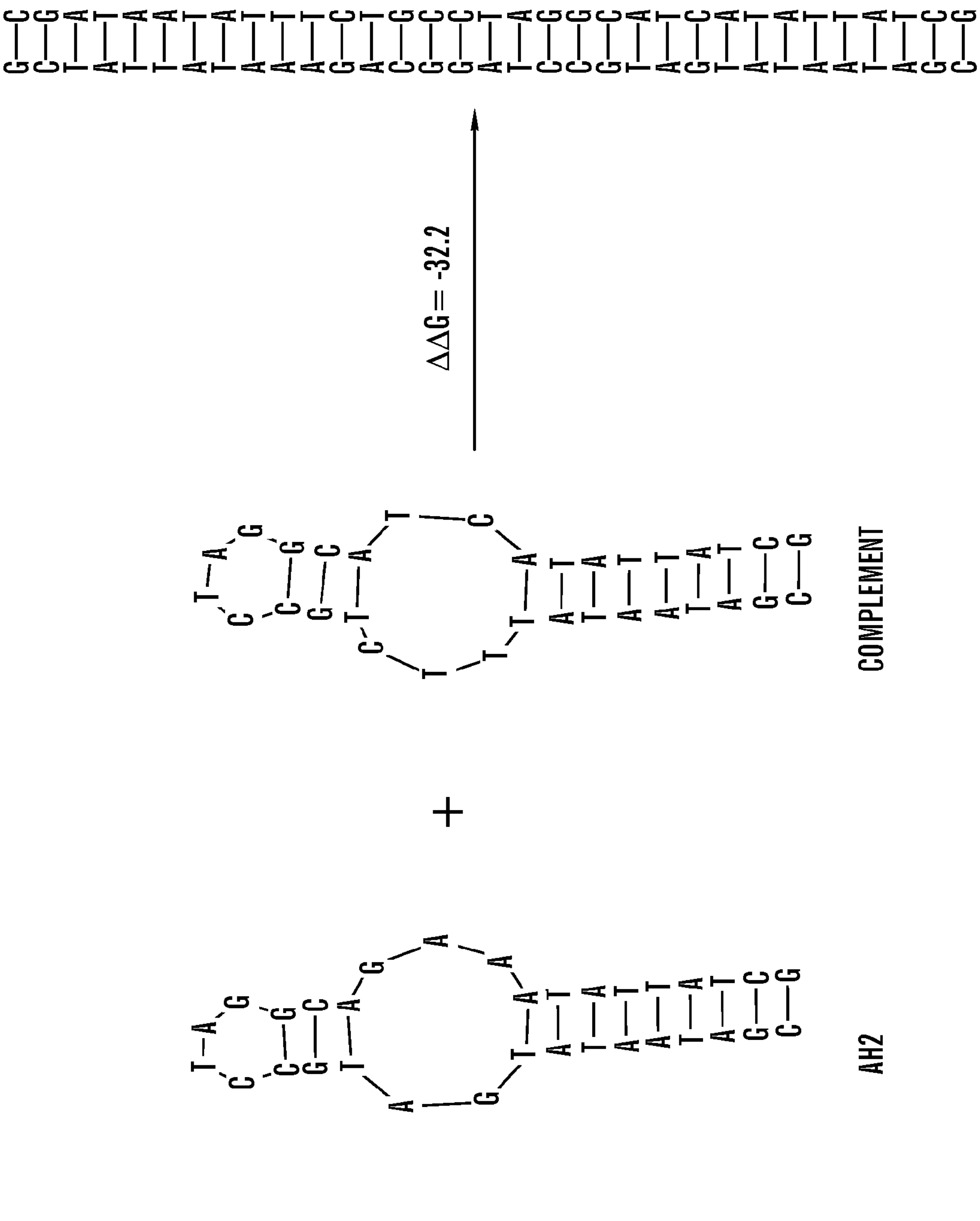
Figure 8D:
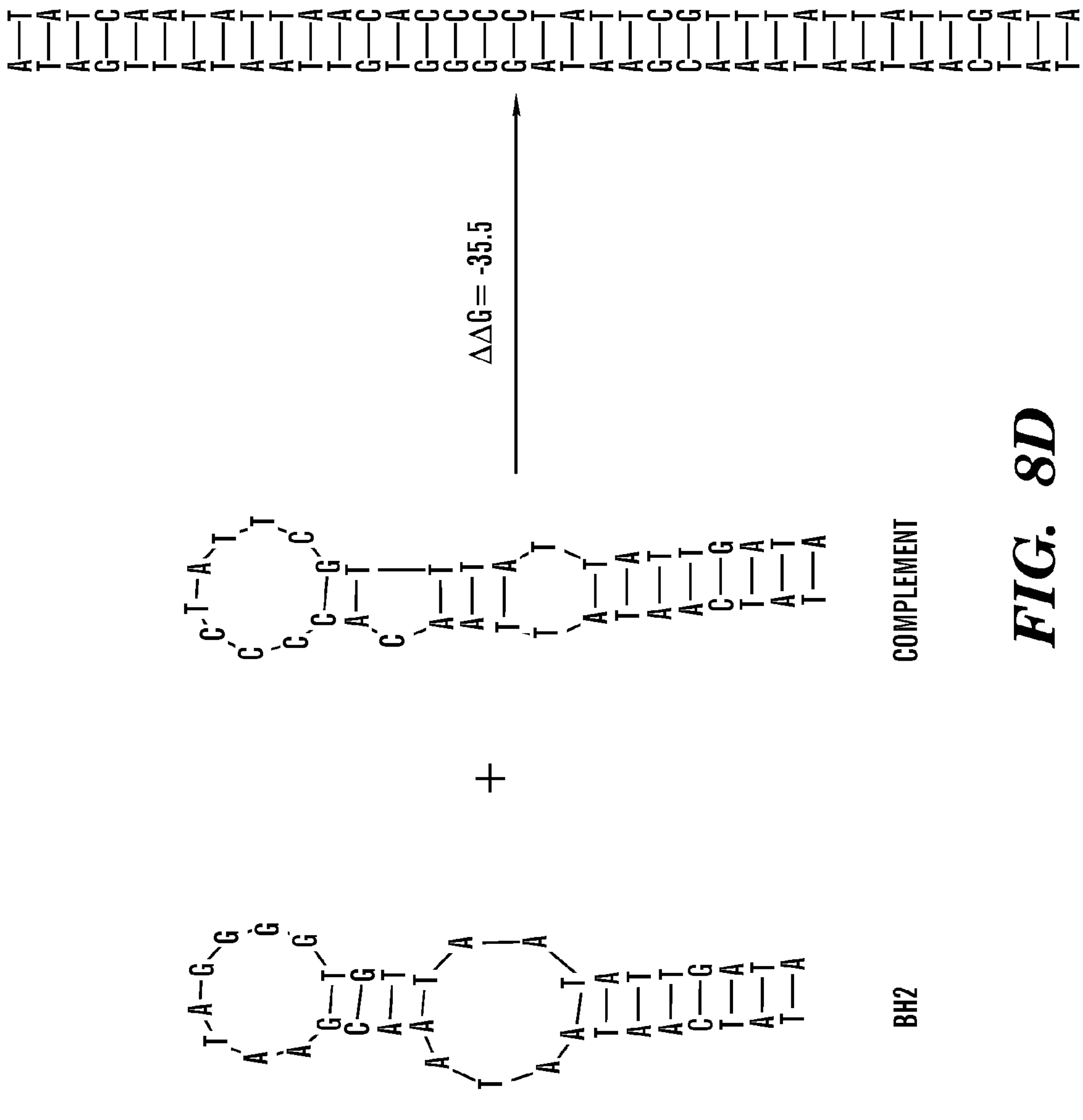

Having selected AH2 and BH2, a final structural prediction of the duplexes (AH2 and BH2 with their respective complements) was carried out to determine their ΔΔG value. The duplex containing AH2 was predicted to have a free energy value of −32.2 kcal/mol and the duplex containing BH2 was predicted to have a free energy value of −35.5 kcal/mol (FIGS. 8C-D). These values indicate that the hybridization between the hairpin and its target will be an energetically favorable process. A BLAST search was independently performed using the AH2 and BH2 sequences, the results indicating that only segments of the *Staphylococcus aureus* genome contain highly related nucleotide sequences.

Example 3

Hairpins Targeted to Other Pathogen

This process described above and exemplified in Examples 1-2 has also been performed using *Exophiala dermatitidis* 18S ribosomal RNA gene sequences to identify hairpin probes that can be used to identify the target gene (and organism); *Trichophyton tonsurans* strain 18S ribosomal RNA gene sequences to identify hairpin probes that can be used to identify the target gene (and organism); and *Bacillus cereus* genomic DNA to identify hairpin probes that can be used to identify the target DNA (and organism). These sequences have been reported in PCT Patent Application to Miller et al., entitled "Hybridization-Based Biosensor Containing Hairpin Probes and Use Thereof," filed Jan. 2, 2003, now WO 2004/061127, which is hereby incorporated by reference in its entirety.

Example 4

Hairpins Favorably Hybridize with their Target DNA

Figure 9:
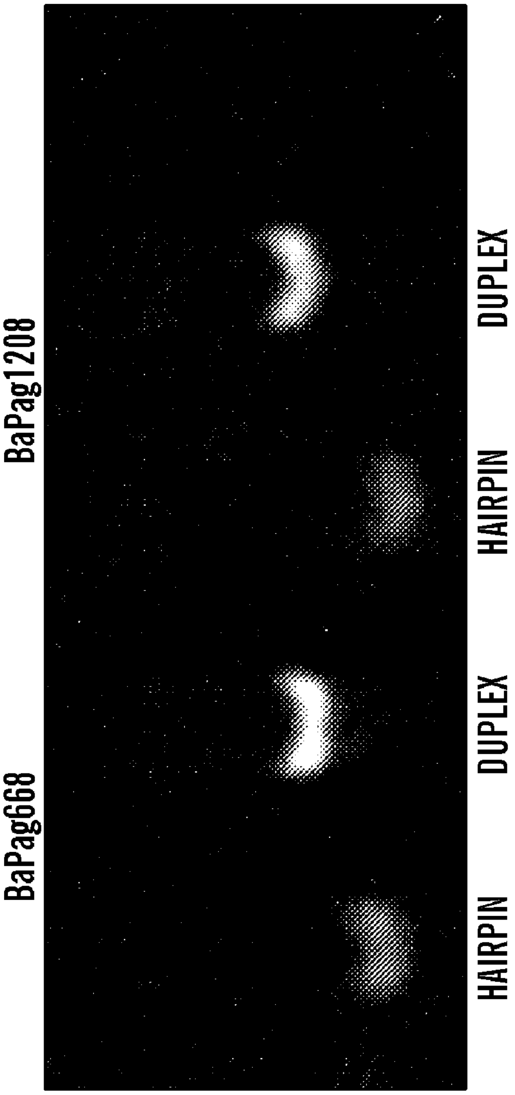
FIG. 9 demonstrates that hairpins favorably hybridize with their target DNA. Samples of BaPag668 (BaPag668-706) and BaPag12O8 (BaPag1208-1241), both alone and mixed with equal amount of complement, were run on a native polyacrylamide gel. The presence of single bands in Lanes 1 and 3 is evidence that the hairpins preferentially adopt one structure because any variations from the predicted structure would either enhance or retard the variant's migration through the gel, thus creating multiple bands. The upward shift seen in Lanes 2 and 4 is indicative of the addition of mass that occurs during the hybridization of the hairpins with their targets. The increased contrast of the bands in Lanes 2 and 4 also gives indication that the hairpins are successfully forming double-stranded duplexes with their targets, as the dye used preferentially binds double-stranded regions of DNA.
Figure 10A:
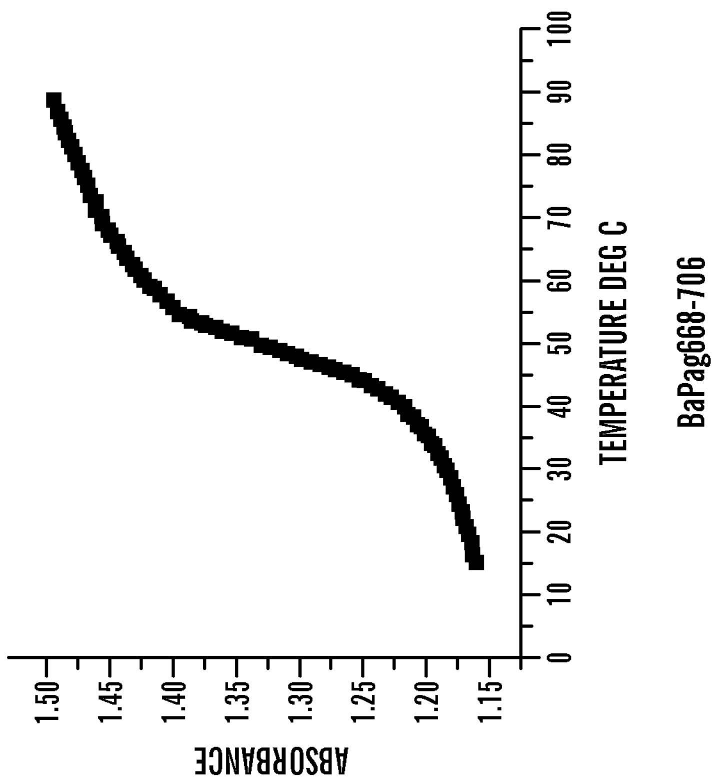
FIGS. 10A-H show the thermal melting curves for DNA hairpin probes. Unmodified versions of BaPag668-706, BaPag1208-1241, AH2, BH2, and their complements were purchased from Invitrogen (cartridge purity). All thermal melts were conducted on a Gilford spectrophotometer, with the oligonucleotides dissolved in 0.5 M NaCl Buffer (20 mM cacodylic acid, 0.5 mM EDTA, and 0.5 M NaCl, pH=7.28). Samples were warmed to 90° C. and subsequently cooled to 10° C. prior to running melts. Solution temperatures were raised by 1° C. per minute over a range of 15° C. to 90° C. and data points were collected approximately every 30 s (FIGS. 10A-D). All melting temperatures (x-axis) of BaPag668-706, BaPag1208-1241, AH2, and BH2 were found to be concentration independent (absorbance is indicated on the y-axis). The unmodified hairpins were then mixed with a ten-fold excess of complementary DNA and a second series of melting profiles were obtained (FIGS. 10E-H). As was expected, introduction of complement to the hairpins produced a biphasic transition curve, with the first transition corresponding to the linearization of the target DNA, which is also believed to possess ordered secondary structure, and the second, higher temperature, transition corresponding to the melting point of the duplex DNA.
Figure 10B:
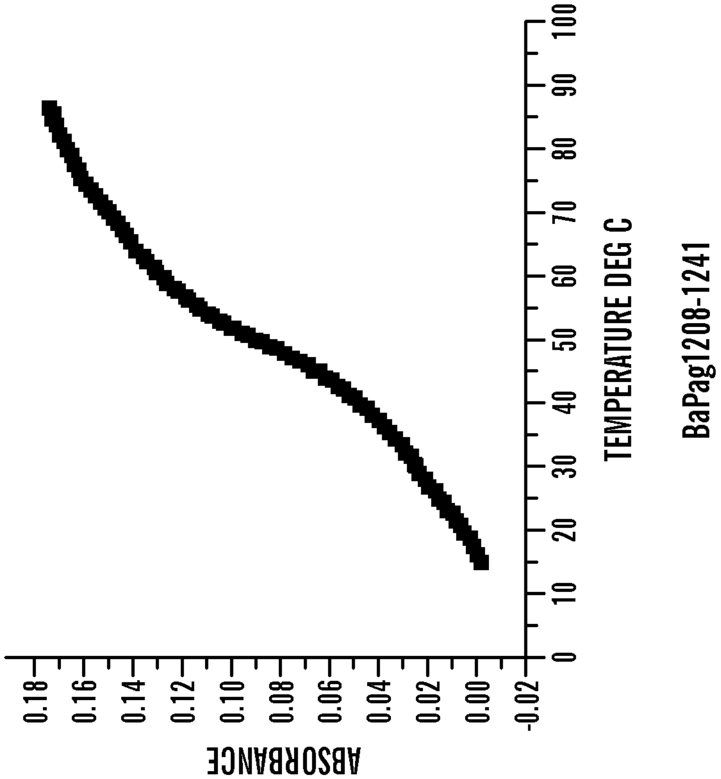
Figure 10D:
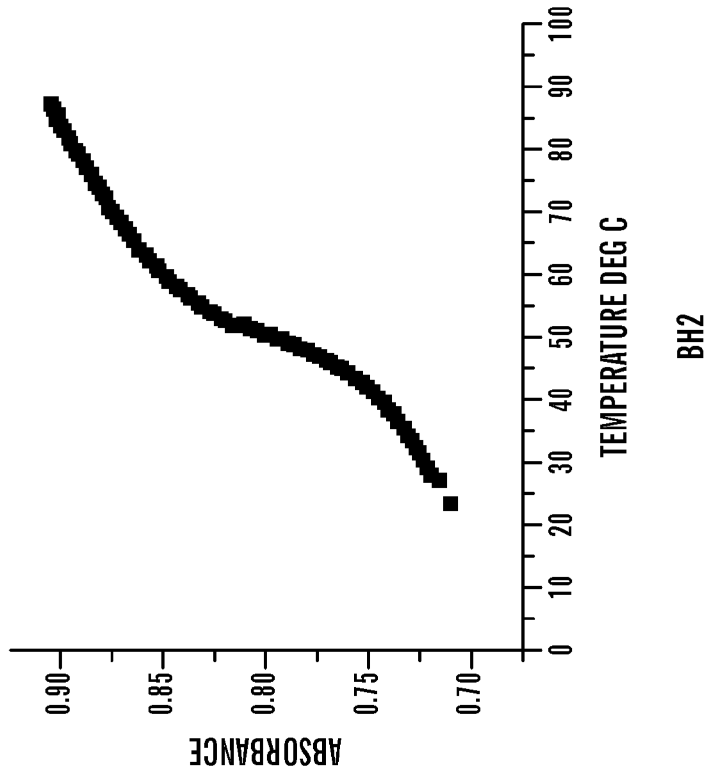
Figure 10C:
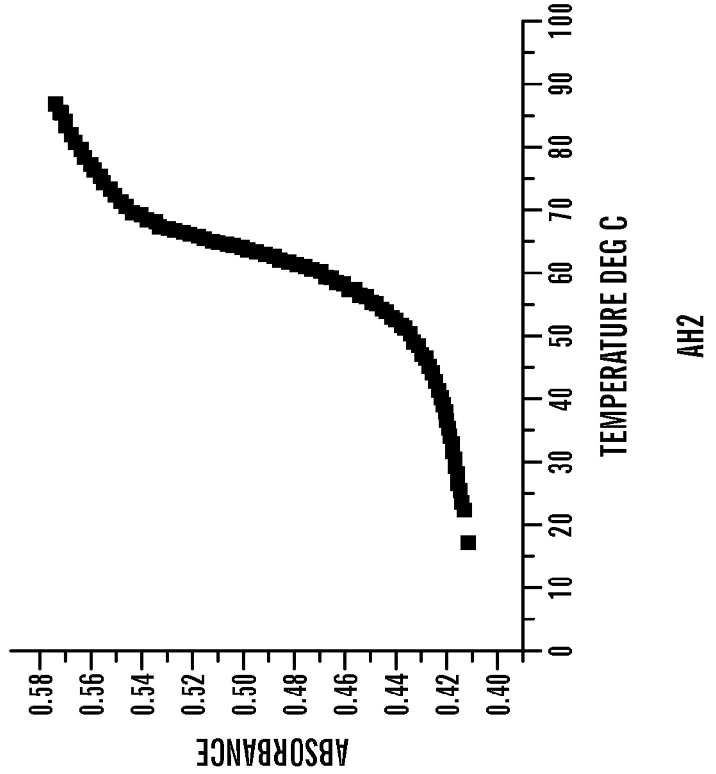
Figure 10E:
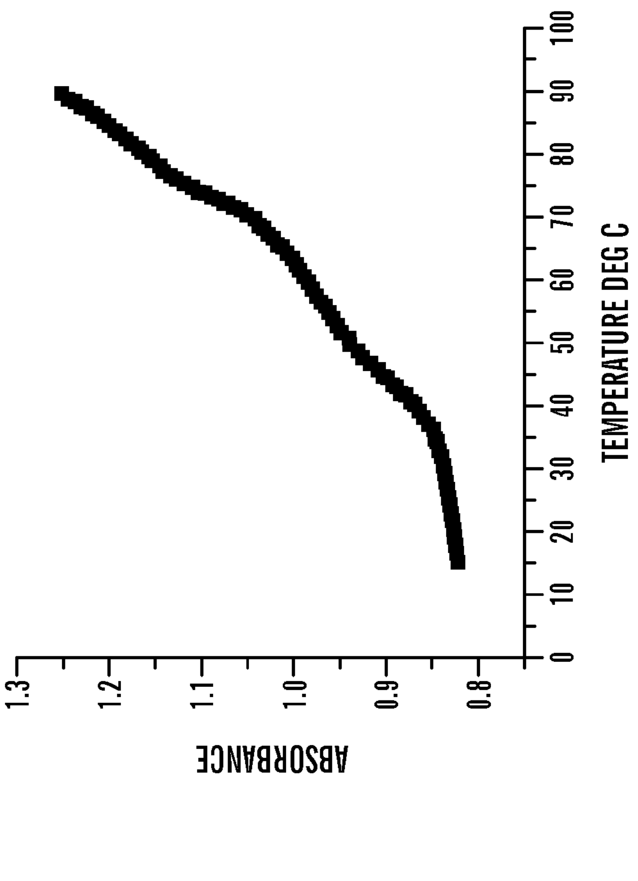
Figure 10F:
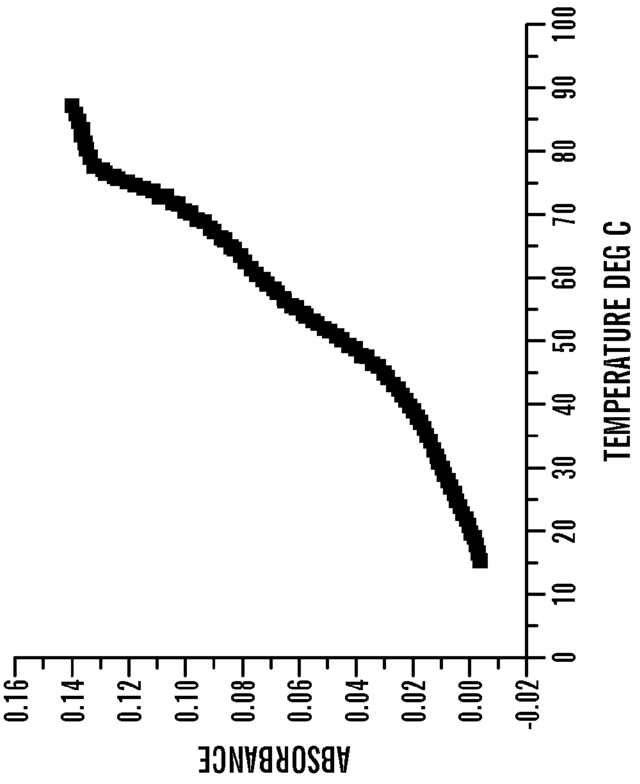
Figure 10G:
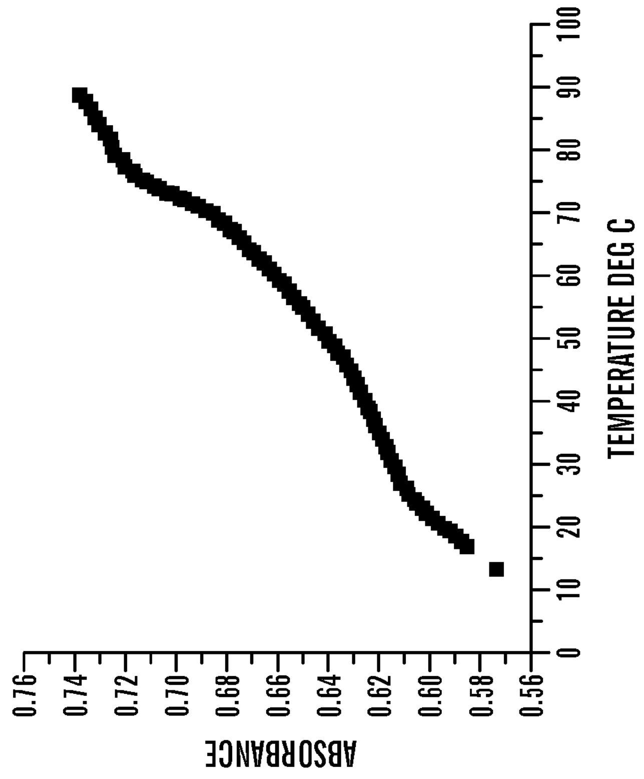
Figure 10H:
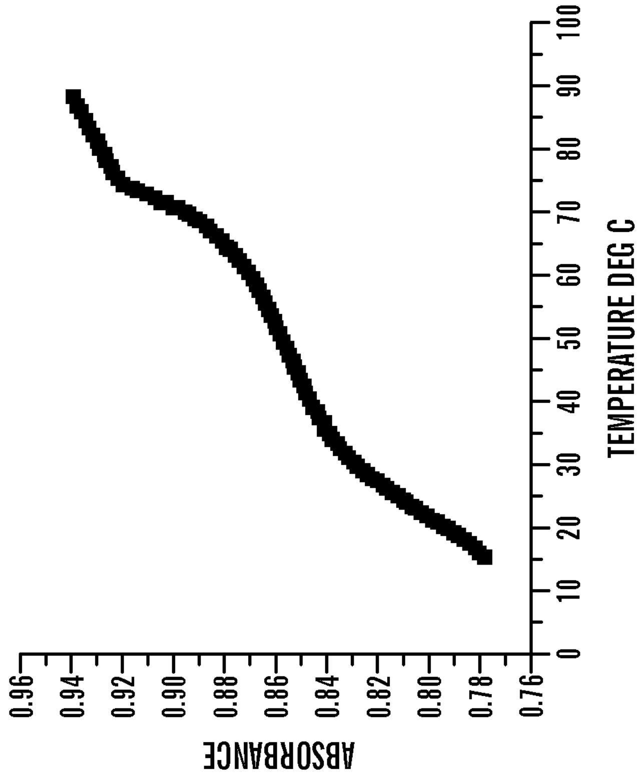

Samples of BaPag668 and BaPag1208, both alone and mixed with equal amount of complement, were run on a native polyacrylamide gel. The purpose of this experiment was two-fold: (1) to demonstrate that, as predicted, the designed hairpins form only one preferred structure, and (2) to provide another example that the hairpins will favorably hybridize with their target DNA. The results are shown in FIG. 9.

The presence of single bands in Lanes 1 and 3 is evidence that the hairpins preferentially adopt one structure. This claim can be made confidently because the distance non-duplexed DNA migrates through a polyacrylamide gel is based on both the size (molecular weight) and shape of the molecule in question. Any variations from the predicted structure would either enhance or retard the variant's migration through the gel, thus creating multiple bands.

The upward shift seen in Lanes 2 and 4 is indicative of the addition of mass that occurs during the hybridization of the hairpins with their targets. The increased contrast of the bands in Lanes 2 and 4 also gives indication that the hairpins are successfully forming double-stranded duplexes with their targets, as the dye used preferentially binds double-stranded regions of DNA.

Example 5

Thermal Melting Curves for DNA Hairpin probes

Determination of the presence of an ordered secondary structure was accomplished via the procurement of thermal melting profiles. All melting temperatures of BaPag668-706, BaPag1208-1241, AH2, and BH2 were found to be concentration independent. As discussed by others (Inglesby et al., "Anthrax as a Biological Weapon: Medical and Public Health Management," *J. Am. Med. Assoc.* 281:1735-1745 (1999), which is hereby incorporated by reference in its entirety), the observed concentration independence is a strong indicator of the presence of an ordered secondary structure, presumed to be the desired hairpins. The unmodified hairpins were then mixed with a ten-fold excess of complementary DNA and a second series of melting profiles were obtained (FIGS. 10E-H). As was expected, introduction of complement to the hairpins produced a biphasic transition curve, with the first transition corresponding to the linearization of the target DNA, which is also believed to possess ordered secondary structure, and the second, higher temperature, transition corresponding to the melting point of the duplex DNA.

Example 6

Solution-phase Performance of Beacon BaPag668-706

Figure 11:
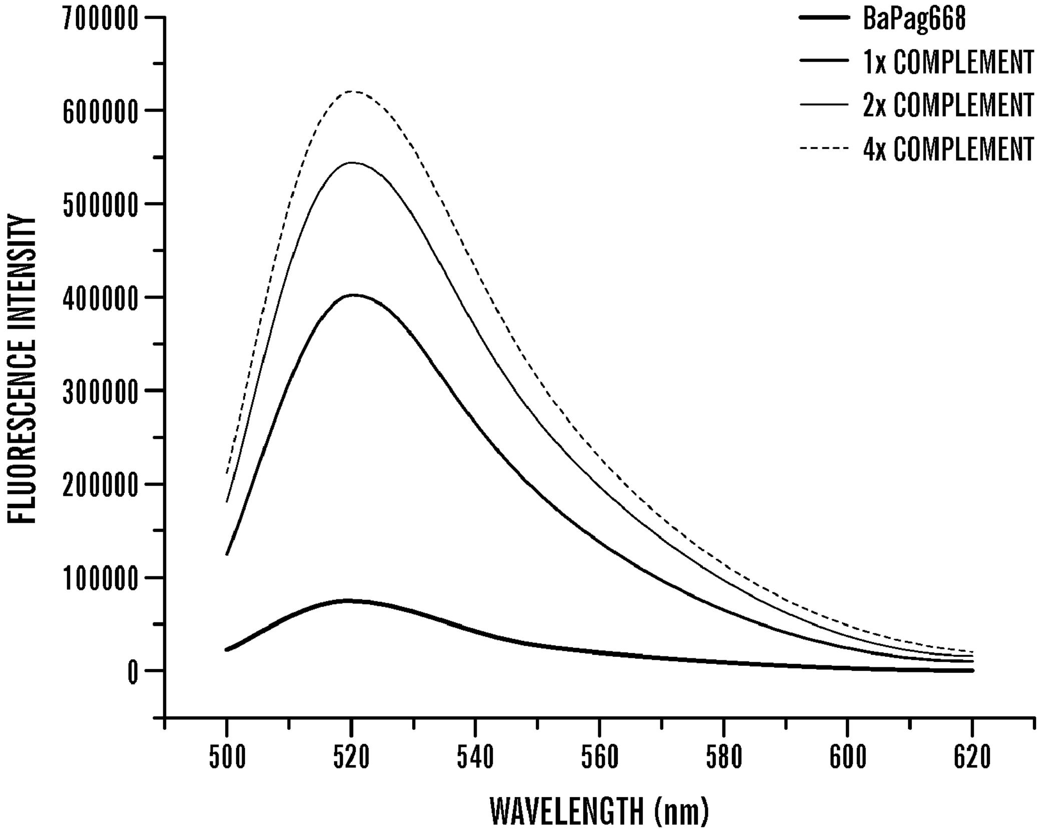
FIG. 11 shows the solution phase performance of the BaPag668-706 probe. BaPag668-706 was purchased from Integrated DNA Technologies, Inc. as a molecular beacon using 5'-fluorescein and 3'-dabcyl as the fluorophore and quencher, respectively. BaPag668-706 was diluted to a concentration of 300 nM in 0.5 M NaCl Buffer (20 mM Cacodylic acid, 0.5 mM EDTA, and 0.5 M NaCl, pH=7.28), to which target DNA was then added such that the final ratio of target to beacon ranged from 1:1 to 4:1. Samples were allowed to incubate 5 hours at room temperature and were kept out of direct light as much as possible prior to excitation to prevent photobleaching. Samples were transferred to a Starna Cells 23-Q-10 Quartz fluorometer cell (10 mm pathlength) and placed on an Acton Research Instruments Fluorometer System. The fluorophore was excited at 490 nm and the resulting emission was monitored from 500 to 620 nm (x-axis). BaPag668-706 exhibits minimal fluorescence alone, and, as expected, addition of the target complementary oligonucleotide causes fluorescence to increase in a concentration-dependent manner.

To provide an initial indication of the ability of the BaPag668-706 probe to function as a molecular beacon, the response to target DNA of BaPag668-706 when modified with a 5'-fluorescein and a 3'-dabcyl. The modified BaPag668-706 beacon was mixed with increasing concentrations of target DNA in aluminum foil covered eppendorf tubes. After approximately one hour at room temperature, fluorescence measurements were procured to determine the efficacy of the beacon. As shown in FIG. 11, BaPag668-706 exhibits minimal fluorescence alone, and, as expected, addition of the target complementary oligonucleotide causes fluorescence to increase in a concentration-dependent manner.

Example 7

Performance of BaPag1208 Immobilized on an Au-film

Figure 12C:
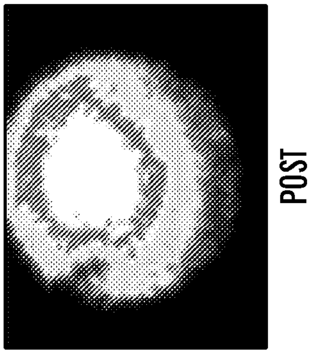
FIGS. 12A-F show the performance of the BaPag1208-1241 probe immobilized in a 1:10 ratio with mercaptopropanol on an Au-film. The 5'-thiol terminated version of BaPag1208-1241 was immobilized on a thin Au film in the presence of mercaptopropanol as described previously (Du et al., "Hybridization-based Unquenching of DNA Hairpins on Au Surfaces: Prototypical "Molecular Beacon" Biosensors, "*J. Am. Chem. Soc.*, 125:4012:4013 (2003), which is hereby incorporated by reference in its entirety) with the only major change being the use of 0.5 M NaCl buffer as the diluent as opposed to deionized water. When immobilized on an Au-film in a 1:10 ratio with mercaptopropanol, BaPag1208-1241 shows greater than an 18-fold increase in fluorescence intensity (y-axis) in response to incubation in a 2.5 μM target solution (FIGS. 12A-C). When the concentration of the target solution is lowered to 1.0 μM, the observed response drops to about 10-fold, which is still significant (FIGS. 12D-F).
Figure 12B:
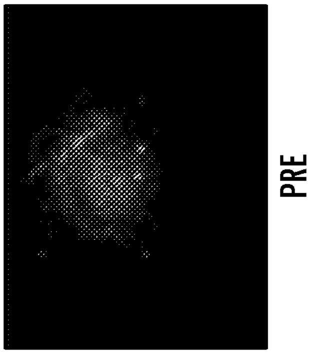
Figure 12A:
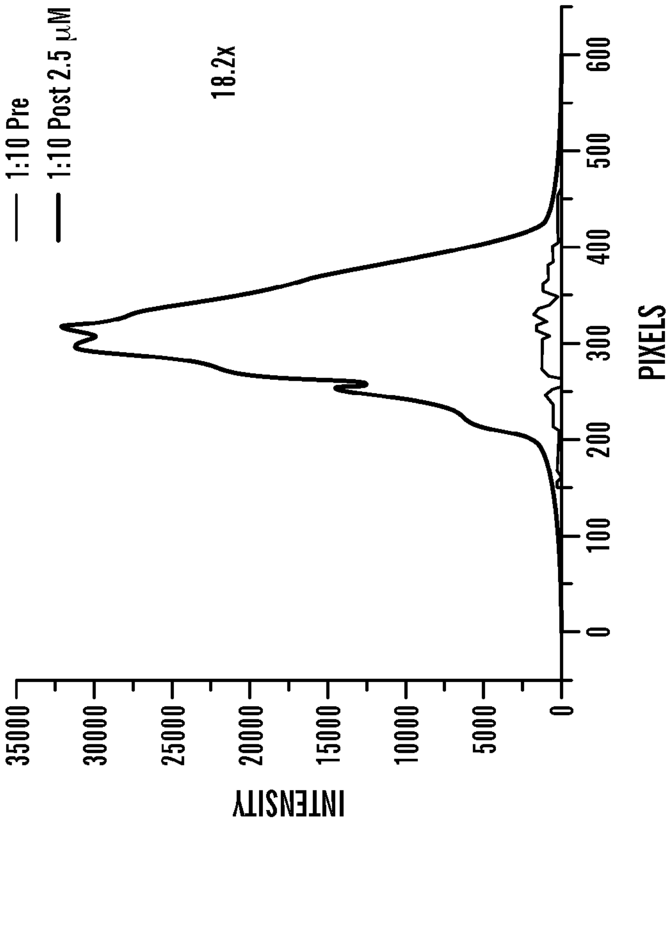

The performance of the functionalized hairpins as Au-immobilized DNA sensors was examined. BaPag1208 was immobilized onto an Au film in much the same manner as has previously been reported (Du et al., "Hybridization-based Unquenching of DNA Hairpins on Au Surfaces: Prototypical "Molecular Beacon" Biosensors," *J. Am. Chem. Soc.* 125: 4012:4013 (2003), which is hereby incorporated by reference in its entirety), with the only major change being the use of 0.5 M NaCl buffer as the diluent as opposed to deionized water. BaPag1208 was initially immobilized in a 1:10 ratio with mercaptopropanol, the results of which are shown in FIGS. 12A-C.

Figure 12F:
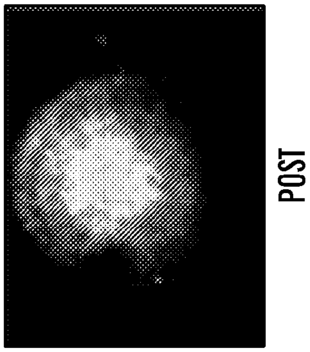
Figure 12E:
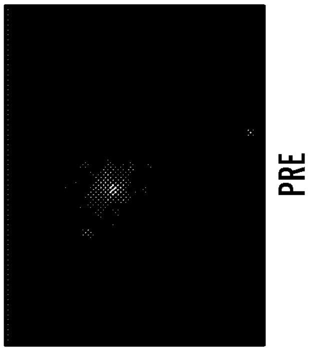
Figure 12D:
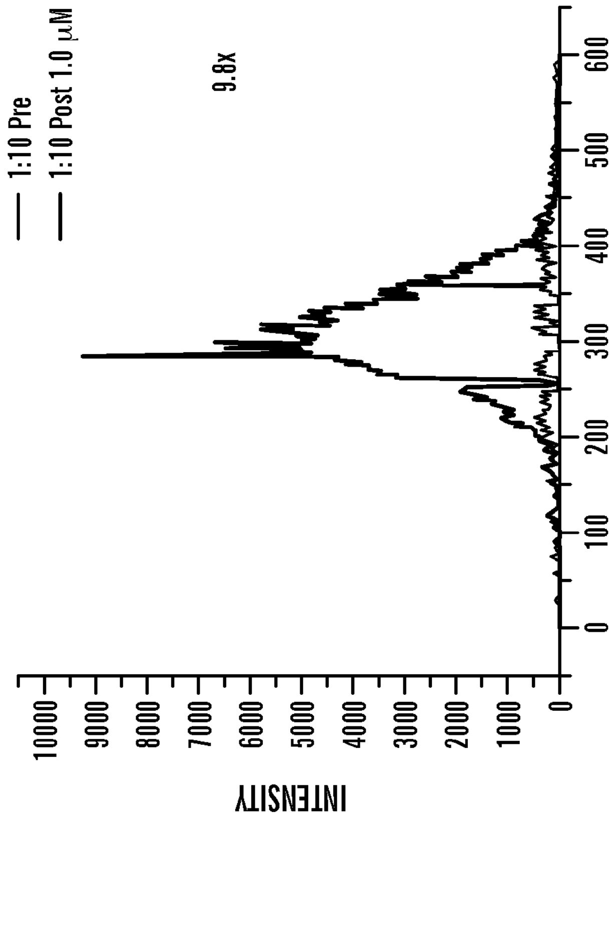

When immobilized on an Au-film in a 1:10 ratio with mercaptopropanol, BaPag1208 shows greater than an 18-fold increase (FIGS. 12A-C) in fluorescence intensity in response to incubation in a 2.5 μM target solution. When the concentration of the target solution is lowered to 1.0 μM, the observed response drops to about 10-fold, which is still significant (FIGS. 12D-F).

Figure 13A:
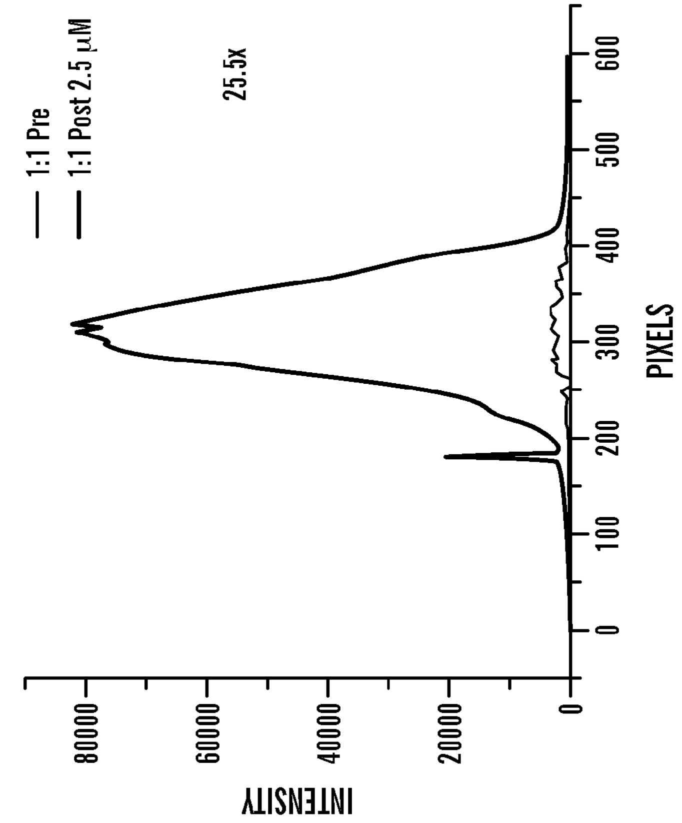
FIGS. 13A-F show the performance of the BaPag1208-1241 probe immobilized in a 1:1 ratio with mercaptopropanol on an Au-film. BaPag1208-1241 was immobilized onto an Au-film with mercaptopropanol in a 1:1 ratio and subjected to the same target concentrations as described previously.
Figure 13B:
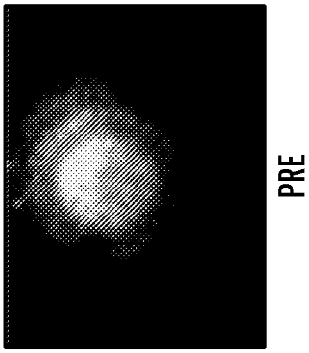
Figure 13C:
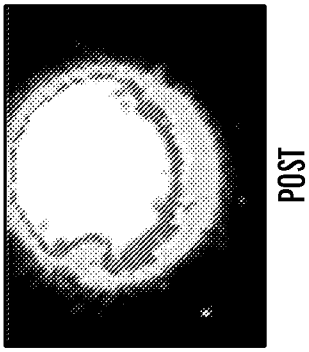
Figure 13D:
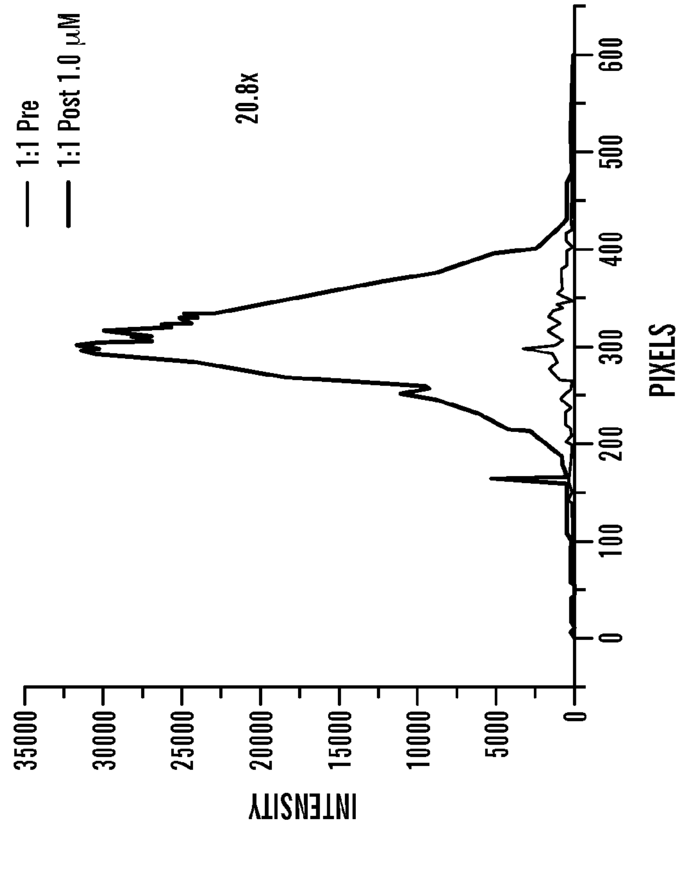
Figure 13E:
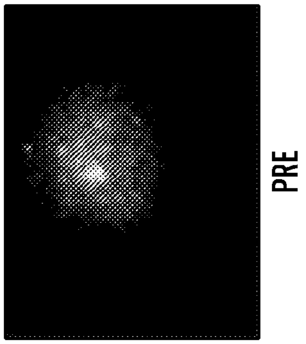
Figure 13F:
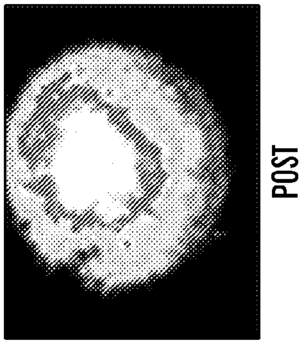

Despite reports that 1:10 ratio of beacon to mercaptopropanol provided for the best signal to noise ratio for more traditional beacons, additional studies suggested that for BaPag1208, a 1:1 ratio may provide a more effective beacon. As such, BaPag1208 was immobilized onto an Au-film with mercaptopropanol in a 1:1 ratio and subjected to the same target concentrations as described previously. As can be clearly seen in FIGS. 13A-C, when immobilized in a 1:1 ratio with mercaptopropanol, BaPag1208 shows a superior response to target over that observed when the immobilization ratio is 1:10. This increased response is especially significant at lower concentrations as is evidenced by the greater than 20-fold intensity increase observed after incubation in 1.0 μM target. (FIG. 13D-F).

Figure 14:
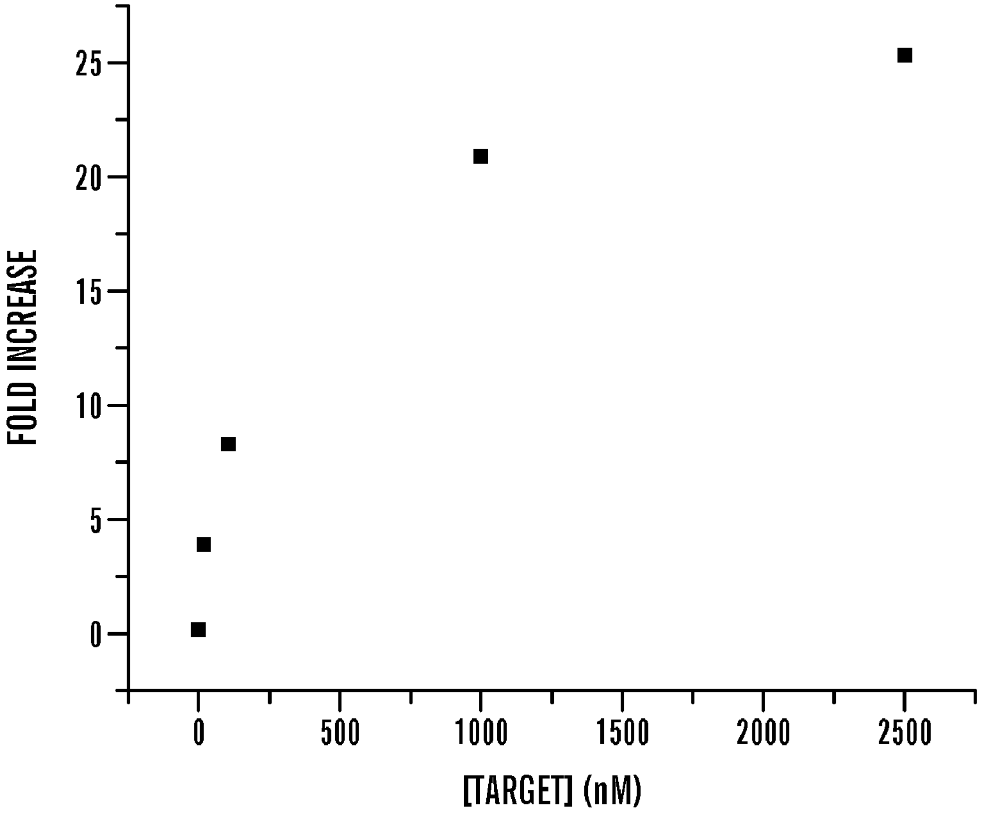
FIG. 14 summarizes the sensitivity of BaPag1208-1241 to a target sequence when immobilized onto an Au-film. The nanomolar target concentration is depicted on the x-axis. The fold increase in binding of BaPag1208-1241 to a target sequence is depicted on the y-axis.

Initial studies as to the sensitivity of BaPag1208-1241 when immobilized onto an Au-film have been started and are summarized in FIG. 14. BaPag1208-1241 immobilized beacons have shown a nearly a 10-fold response to a 1.0 mL solution of 1.0 nM target (1.0 pmol). Studies planned for the very near future should elucidate the absolute limit of detection for a solution of synthetic and native targets.

Example 8

Performance of AH2 and BH2 Immobilized on an Au-film

Figure 15A:
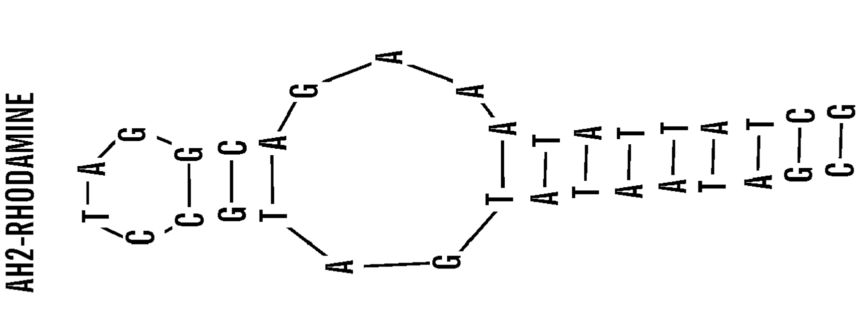
FIGS. 15A-F show the use of Au-immobilized AH2 and BH2 beacons to detect complementary DNA sequences. The AH2 and BH2 hairpins were 3'-modified with tetramethylrhodamine ("TAMRA") and Cy5, respectively. Each probe was dissolved separately in a solution of mercaptopropanol and water (1:10 molar ratio of probe and mercaptopropanol). The resulting probe solutions were then mixed in a 1:1 ratio, added to Au-chips and measurements of baseline fluorescence made (FIGS. 15B and 15E). The Au-films were then separately incubated in their appropriate complementary target solutions and fluorescence measured (FIGS. 15C and 15F). The fluorescence demonstrated in FIGS. 15C and 15F indicate that AH2 and BH2 probe beacons effectively detect complementary DNA sequences.
Figure 15B:
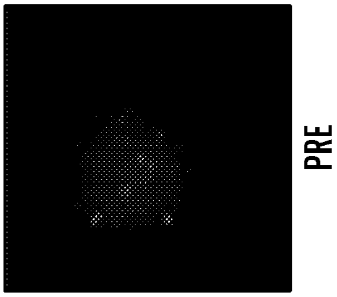
Figure 15C:
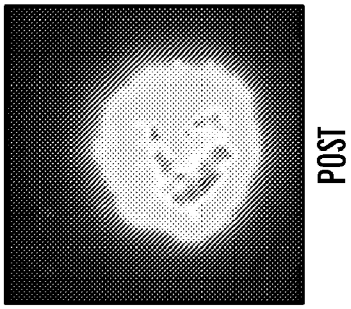
Figure 15F:
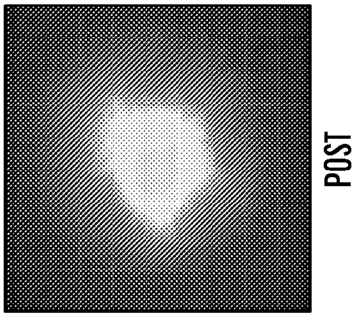
Figure 15E:
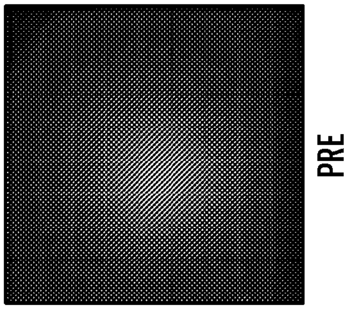
Figure 15D:
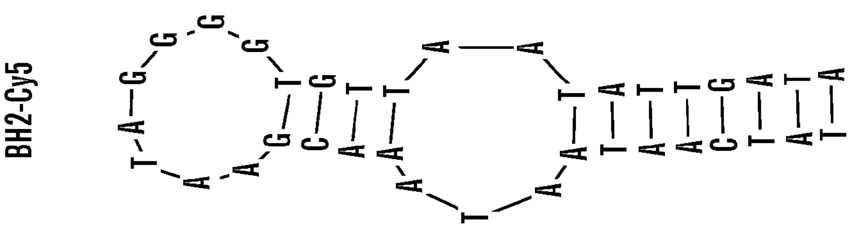

To examine the suitability of the "partial gene folding" derived beacons in such a scheme, the *Staphylococcus aureus* probes AH2 and BH2 were obtained modified with a 5'-thiol (allowing for attachment to Au film using standard chemistry), and either a 3'-rhodamine (AH2) or a 3'-Cy5 (BH2). These two probes were concurrently assembled in a 1:1 ratio in the presence of mercaptopropanol on two Au films. Individual films were then treated with solutions of either AH2-complement or BH2-complement. Addition of 1.0 μM AH2-complement yielded a chip with significant fluorescence around 585 nm (FIG. 15C), while addition of 1.0 μM BH2-complement produced weak, but still observable Cy5 fluorescence (675 nm) (FIG. 15F). A partial reason for the weak signal observed from the Cy5 is due to the small absorption cross section for Cy5 in green wavelengths. Indeed, using an AH2-Cy5 functionalized surface, excitation at 633 nm (cross section 8 times greater than at 514 nm) produced twice as much fluorescence intensity from Cy5. These results suggest that although differentiating multiple targets with only a single light source is not yet optimized, co-immobilization of two probes produces a functional chip.

Example 9

Calculated Hybridization Energies for Folding-derived and Modified Beacons

Figures 16A, 16B, 16C:
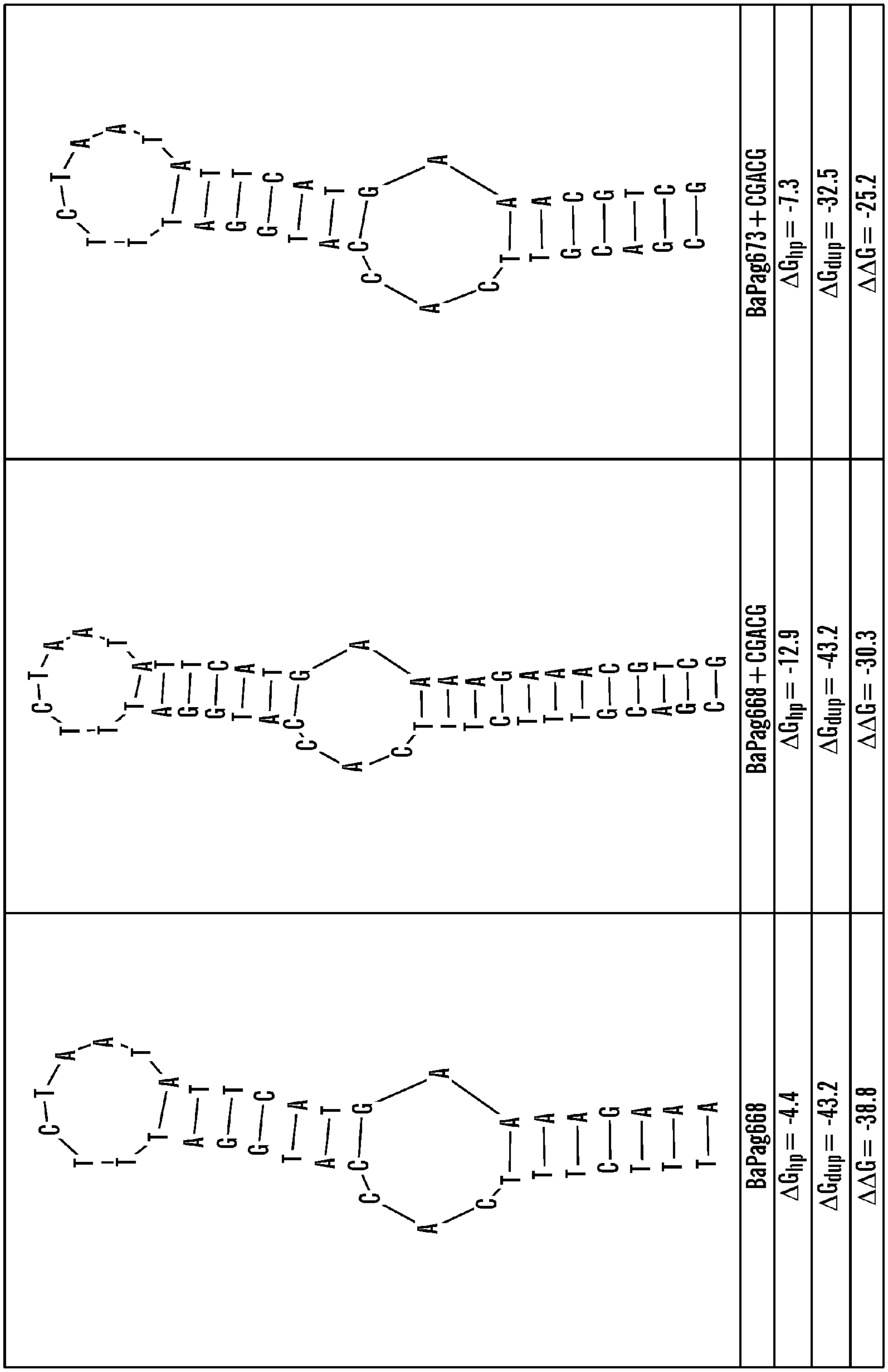
FIGS. 16A-C show the calculated hybridization energies for folding-derived and modified BaPag668-706 beacons.
Figures 17A, 17B, 17C:
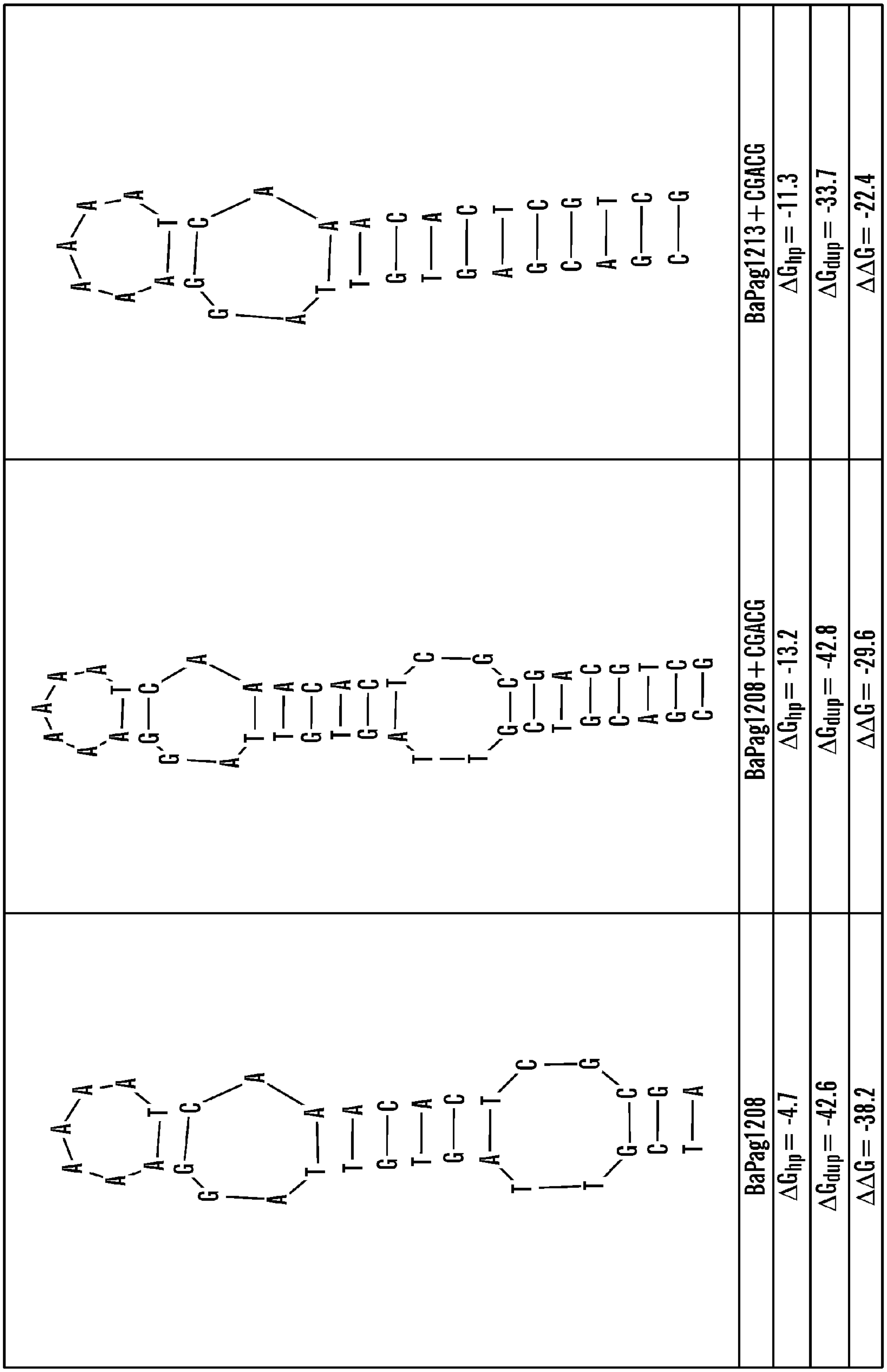
FIGS. 17A-C show the calculated hybridization energies for folding-derived and modified BaPag1208-1241 beacons.

It is difficult to rigorously compare folding-derived to modified beacons, since changing the sequence obviously alters more than one experimental parameter. However, the effects of modification can be predicted, as shown by the calculations in FIGS. 16 and 17. The termini of probes BaPag668-706 and BaPag1208-1241 were first extended by the self-complementary sequence $[d(CGACG)]_2$, then the hybridization energy calculated (FIGS. 16B and 17B, resepectively). Second, five bases were removed from each end of BaPag668-706 and BaPag1208-1241, replaced with $[d(CGACG)]_2$, and the hybridization energy again calculated (FIGS. 16C and 17C, respectively). In each case, calculated ΔΔG values were less favorable for the modified beacons than for the probes derived directly from folding.

The fact that the hybridization product of the new beacon is energetically superior to that of the traditional design should lead the new beacon to have a higher sensitivity. The binding free energy for hybridization $\Delta G_{bind}$ is related to the observed equilibrium association constant $K_A$ by: $-\Delta G_{bind}=-RT\ln K_A$, where T is the temperature and R the universal gas constant (Riccelli et al.,"Hybridization of Single-stranded DNA Targets to Immobilized Complementary DNA Probes: Comparison of Hairpin Versus Linear Capture Probes," *Nucl. Acids Res.* 29: 996-1004 (2001), which is hereby incorporated by reference in its entirety). The use of hairpins that have 100% sequence participation in duplex formation allows for a more energetically favorable duplex than would exist for a hairpin that contains non-specific termini. Thus, the duplex that forms the more energetically favorable dimer will be expected to bind much more tightly, and therefore is expected to be more sensitive. Highly sensitive detection schemes are preferred for rapid detection and identification of pathogens in a clinical sample.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An isolated nucleic acid probe comprising:

a hairpin DNA molecule that hybridizes over its full length to a target nucleic acid that has a naturally occurring sequence;

a label tethered to one terminus of the hairpin DNA molecule; and a quenching agent tethered to the other terminus of the hairpin DNA molecule.

2. The isolated nucleic acid probe according to claim 1, wherein the label is tethered to the 5' terminus and the quenching agent is tethered to the 3' terminus.

3. The isolated nucleic acid probe according to claim 1, wherein the label is tethered to the 3' terminus and the quenching agent is tethered to the 5' terminus.

4. The isolated nucleic acid probe according to claim 1, wherein the quenching agent is a solid surface.

5. The isolated nucleic acid probe according to claim 1, wherein the quenching agent is a micro- or nano-particle.

6. The isolated nucleic acid probe according to claim 1, wherein the label is a fluorescent dye, semiconductor quantum dot, lanthanide atom-containing complex, or fluorescent protein.

7. The isolated nucleic acid probe according to claim 1, wherein the quenching agent is a metal or 4-([4-(Dimethylamino)phenyl]azo)benzoic acid.

8. The isolated nucleic acid probe according to claim 7 wherein the metal is gold, silver, platinum, copper, cobalt, iron, or iron—platinum.

9. The isolated nucleic acid probe according to claim 1, wherein the hairpin DNA molecule is characterized by a predicted E value of at most about 3 kcal/mol.

10. The isolated nucleic acid probe according to claim 9, wherein the predicted E value is between about—4 kcal/mol and about 12 kcal/mol.

11. The isolated nucleic acid probe according to claim 1, wherein the hairpin DNA molecule is between about 12 and about 60 nucleotides in length.

12. The isolated nucleic acid probe according to claim 1, wherein hybridization between the hairpin DNA molecule and a target nucleic acid sequence is predicted to have a lowest free energy value that is at least about a two-fold increase over the lowest predicted energy value of the hairpin DNA molecule alone.

13. The isolated nucleic acid probe according to claim 1, wherein the hairpin DNA molecule includes first and second portions that hybridize to form a stem when the hairpin DNA molecule is in a hairpin configuration, and the first and second portions contain no exogenous nucleotides.

14. The isolated nucleic acid probe according to claim 1, wherein the hairpin DNA molecule consists of a nucleotide sequence that is 100% complementary to a target nucleic acid sequence.

15. A method of detecting a target nucleic acid molecule in a sample comprising:

providing a sample that may contain a target nucleic acid molecule having a target nucleic acid sequence;

introducing the isolated nucleic acid probe of claim 1 into the sample; and determining whether the label can be detected within the sample, wherein detection of the label indicates the presence of the target nucleic acid molecule in the sample.

16. The method according to claim 15, wherein said determining comprises:

exposing the sample comprising the isolated nucleic acid probe to a source of light suitable to induce fluorescent emissions by the label; and measuring fluorescent emissions by the label.

17. An isolated DNA molecule comprising first and second regions that are capable of self-hybridizing, under appropriate conditions, into a hairpin configuration, wherein the DNA molecule has a nucleotide sequence that hybridizes over its full length to a target nucleic acid that has a naturally occurring sequence.

18. The isolated DNA molecule according to claim 17, wherein the DNA molecule consists of a nucleotide sequence that is 100% complementary to a the target nucleic acid sequence.

19. The isolated DNA molecule according to claim 17, wherein the DNA molecule is complementary to the target nucleic acid sequence and contains no exogenous nucleotides.

20. The isolated nucleic acid molecule according to claim 17, wherein the DNA molecule contains between about 12 and about 60 nucleotides.

21. The isolated nucleic acid probe according to claim 1, wherein the hairpin DNA molecule specifically hybridizes over its full length to the target nucleic acid.

* * * * *